(12) United States Patent
Watanabe et al.

(10) Patent No.: US 8,394,481 B2
(45) Date of Patent: Mar. 12, 2013

(54) OPTICAL INFORMATION RECORDING MEDIUM AND AZO METAL COMPLEX DYE

(75) Inventors: Kousuke Watanabe, Minami-ashigara (JP); Taro Hashizume, Minami-ashigara (JP); Kazutoshi Katayama, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 961 days.

(21) Appl. No.: 12/443,315

(22) PCT Filed: Sep. 28, 2007

(86) PCT No.: PCT/JP2007/068969
§ 371 (c)(1),
(2), (4) Date: Mar. 27, 2009

(87) PCT Pub. No.: WO2008/038765
PCT Pub. Date: Apr. 3, 2008

(65) Prior Publication Data
US 2010/0074082 A1     Mar. 25, 2010

(30) Foreign Application Priority Data

Sep. 28, 2006  (JP) ................. 2006 265692
Apr. 13, 2007  (JP) ................. 2007 106441
Sep. 4, 2007   (JP) ................. 2007 228781

(51) Int. Cl.
B32B 3/02        (2006.01)
G11B 7/24        (2006.01)

(52) U.S. Cl. .............. 428/64.8; 428/64.4; 430/270.16; 534/705

(58) Field of Classification Search .......... 428/64.4, 428/64.8; 430/270.16; 534/705
See application file for complete search history.

(56) References Cited

U.S. PATENT DOCUMENTS

| 4,256,817 | A  | 3/1981  | Hara et al.     |
| 4,271,252 | A  | 6/1981  | Hara et al.     |
| 5,145,963 | A  | 9/1992  | Nagai           |
| 5,633,106 | A  | 5/1997  | Aihara et al.   |
| 7,504,197 | B2 | 3/2009  | Mikoshiba       |
| 7,537,881 | B2 | 5/2009  | Mikoshiba       |
| 2005/0226135 | A1 | 10/2005 | Morita et al.  |
| 2005/0227178 | A1 | 10/2005 | Morita et al.  |
| 2009/0263611 | A1 | 10/2009 | Miyazawa et al. |

FOREIGN PATENT DOCUMENTS

| JP | 58-175693 |   | 10/1983 |
| JP | 11-130970 | A | 5/1999  |
| JP | 11-310728 | A | 11/1999 |
| JP | 2000-168237 | A | 6/2000 |
| JP | 2001-158862 | A | 6/2001 |
| JP | 2001-234154 | A | 8/2001 |
| JP | 2002-274040 | A | 9/2002 |
| JP | 2004-209771 | A | 7/2004 |
| JP | 2005-074852 | A | 3/2005 |
| JP | 2005-162812 | A | 6/2005 |
| JP | 2005-297406 | A | 10/2005 |
| JP | 2005-297407 | A | 10/2005 |
| JP | 2006-142789 | A | 6/2006 |
| JP | 2006-306070 | A | 11/2006 |
| JP | 2007-175968 | A | 7/2007 |
| WO | 2006/061398 | A2 | 6/2006 |
| WO | 2007/007748 | A1 | 1/2007 |

OTHER PUBLICATIONS

Machine translation of JP 2006-142789 (previously submitted IDS of Mar. 27, 2009).
Office Action dated Feb. 21, 2012 in Japanese Application No. 2007-106459, Partial English-Language translation.
Office Action dated Jul. 24, 2012 in Japanese Patent Application No. 2008-536442, English language translation.

*Primary Examiner* — Gerard Higgins
(74) *Attorney, Agent, or Firm* — Sughrue Mion, PLLC

(57) ABSTRACT

A WORM-type recording layer in an optical information recording medium contains at least one azo-metal complex dye derived from a metal ion and a compound represented by the following general formula (1-1) or (1-2):

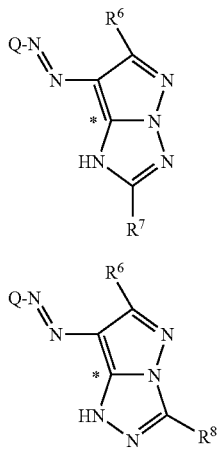

wherein Q represents a carbocyclic group or a heterocyclic group, and $R^6$ to $R^8$ independently represent a hydrogen atom or a substituent. The compound represented by the general formula (1-1) or (1-2) has a dissociative hydrogen atom in Q, and the dissociative hydrogen atom in Q and the hydrogen atom in the —NH— group marked with asterisk * are eliminated from the compound, so that the residue is bonded to the metal ion to generate the azo-metal complex dye. The azo-metal complex dye may contain a component other than the metal ion and the compound represented by the general formula (1-1) or (1-2).

11 Claims, 2 Drawing Sheets

OPTICAL INFORMATION RECORDING MEDIUM AND AZO METAL COMPLEX DYE

TECHNICAL FIELD

The present invention relates to an optical information recording medium for information recording/reproduction using a laser light, and an azo-metal complex dye having a remarkably excellent light fastness. For example, the optical information recording medium is a heat mode-type medium suitable for information recording/reproduction using a laser light having a short wavelength of 440 nm or less, and the azo-metal complex dye is suitable for use in a recording layer of an optical information recording medium.

BACKGROUND ART

Recently Hi-Vision broadcasts and networks such as Internet have been rapidly popularized. Further, in view of upcoming HDTV (High Definition Television) broadcasting, there is an increasing demand for large-capacity recording media for easily recording image information at low costs. Though CD-Rs and DVD-Rs capable of high-density recording using visible laser lights (630 to 680 nm) have been established to some extent as large-capacity recording media, the recording capacities thereof are not sufficiently large for future requirements. Thus, development of optical disks, which utilize laser lights with shorter wavelengths to achieve higher recording densities and larger recording capacities as compared with the DVD-Rs, has been progressed. For example, an optical recording disk utilizing a 405-nm blue laser light, called a Blu-ray disc, has been proposed.

In conventional DVD-R type optical disks, azo-metal complex dyes have been advantageously used as dye compounds in recording layers (see, for example, Patent Documents 1, 2, 3, and 4) These azo-metal complex dyes show absorption waveforms corresponding to red laser lights, and thereby are unsuitable for the 405-nm laser light. Thus, azo-metal complex dyes for the optical recording disk utilizing the 405-nm blue laser light has been studied so as to shorten the absorption wavelengths of the azo-metal complex dyes for the DVD-Rs as disclosed in Patent Documents 5 to 9, etc. However, in Patent Documents 5 to 9, though the maximum absorption wavelengths of solutions or films containing the dyes are described, the light fastness and the recording/reproducing properties in optical information recording media are not described in detail, and the actual storability and the actual recording/reproducing properties are not known.

Films of the azo-metal complexes described in Patent Documents 5 to 9 were evaluated with respect to the light fastness and recording/reproducing properties in the optical information recording media utilizing blue laser lights. As a result, all the films are not satisfactory in both the light fastness and the recording/reproducing properties (the recording sensitivity, 2T CNR).

Patent Document 1: Japanese Laid-Open Patent Publication No. 11-310728
Patent Document 2: Japanese Laid-Open Patent Publication No. 11-130970
Patent Document 3: Japanese Laid-Open Patent Publication No. 2002-274040
Patent Document 4: Japanese Laid-Open Patent Publication No. 2000-168237
Patent Document 5: Japanese Laid-Open Patent Publication No. 2001-158862
Patent Document 6: Japanese Laid-Open Patent Publication No. 2006-142789
Patent Document 7: Japanese Laid-Open Patent Publication No. 2006-306070
Patent Document 8: Japanese Laid-Open Patent Publication No. 2005-297406
Patent Document 9: Japanese Laid-Open Patent Publication No. 2005-297407

DISCLOSURE OF THE INVENTION

In view of the above problems, an object of the present invention is to provide an optical information recording medium having an excellent solubility, excellent recording/reproducing properties, and a remarkably high light fastness (specifically an optical information recording medium capable of information recording by irradiation with a laser light having a wavelength of 440 nm or less), and an azo-metal complex dye useful for forming the optical information recording medium.

Another object of the present invention is to provide an azo-metal complex dye remarkably excellent in light fastness and thermal stability.

In the present invention, a particular azo dye and synthesis method are selected to obtain an anionic azo-metal complex. As for bonds between metal ions and ligands in cationic, neutral, and anionic azo-metal complexes, the degree of covalent bonding is increased in the order of cationic<neutral<anionic, and thus the ligand field splitting is increased in this order (see "Shinpan Sakutai Kagaku (Complex Chemistry, New Edition)", edited by Kiso Sakutai Kogaku Kenkyukai (The Society of Pure & Applied Coordination Chemistry), Kodansha Scientific Ltd., p. 30 to 42). Further, in general, among rings formed by the metal ions and bidentate chelation ligands, 5-membered rings are the most stable (see "Shinpan Sakutai Kagaku (Complex Chemistry, New Edition)", edited by Kiso Sakutai Kogaku Kenkyukai (The Society of Pure & Applied Coordination Chemistry), Kodansha Scientific Ltd., p. 84). Thus, it has been considered that, when a tridentate azo dye (ligand) and a metal ion form two 5-membered rings, the azo dye and metal ion are more strongly bonded to increase the ligand field splitting, whereby the interaction between the $\pi$-$\pi^*$ transition of the azo ligand and the d-d* transition of the metal ion is enhanced. As a result, energy deactivation is efficiently caused in the d-d* transition state of the metal ion, thereby improving the light fastness of the dye.

As a result of intense research based on this idea, the inventors have found that a particular anionic azo-metal complex dye is remarkably excellent in light fastness, solubility, and film stability, and that an optical information recording medium having a recording layer containing the azo-metal complex dye has excellent properties for recording/reproduction by using a blue laser light with a wavelength of 440 nm or less.

The inventors have found that, when a compound represented by the following general formula (1-1) or (1-2) is reacted with a metal compound under basic condition, the resultant azo-metal complex dye has a larger number of metal ions as compared with the conventional azo-metal complex dyes.

Furthermore, the inventors have found that particularly an azo-metal complex having a metal ion/azo dye ligand ratio of 5/4 is further excellent in light fastness and recording/reproducing properties. Thus, Cu ion is more suitable for producing an optical information recording medium excellent in both the light fastness and recording properties than Co and Ni ions, which have been most preferably used. The present invention has been accomplished by the unexpected new findings.

The present invention is advantageously achieved by the following features.

[1] An optical information recording medium according to the present invention, comprising a substrate having pre-grooves with a track pitch of 50 to 500 nm and a recording layer on which information is recorded by irradiation with a laser light having a wavelength of 440 nm or less, wherein the recording layer comprises at least one azo-metal complex dye containing a metal ion and a divalent azo dye anion derived from an azo dye represented by the following general formula (1-1) or (1-2). The azo dye represented by the general formula (1-1) or (1-2) has a dissociative hydrogen atom in Q, and the divalent azo dye anion is provided by eliminating the dissociative hydrogen atom in Q and the hydrogen atom in the —NH— group marked with asterisk * from the azo dye represented by the general formula (1-1) or (1-2) and is bonded to the metal ion to generate the azo-metal complex dye. The azo-metal complex dye may contain a component other than the metal ion and the azo dye represented by the general formula (1-1) or (1-2).

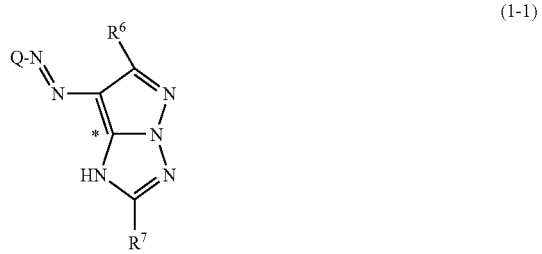
(1-1)

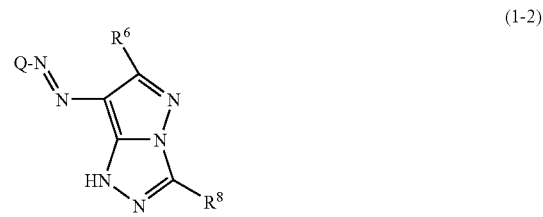
(1-2)

In the general formulae (1-1) and (1-2), Q represents a carbocyclic group or a heterocyclic group. $R^6$ to $R^8$ independently represent a hydrogen atom or a substituent.

[2] An optical information recording medium according to [1], wherein the recording layer comprises at least one azo-metal complex dye represented by the following general formula (A).

   General formula (A)

In the general formula (A), $L^{2-}$ represents a divalent azo dye anion provided by eliminating 2 hydrogen atoms from a compound represented by the following general formula (I-1) or (1-2), L' represents a ligand, M represents a metal ion (or a metal oxide ion), n represents an integer of 1 to 4, m represents an integer of 0 to 3, r represents 1 or 2, $X^{p+}$ represents a p-valent cation, p represents an integer of 1 to 10, and k' represents a value within a range of $0<k'\leq 4$ obtained by dividing the negative charge number in the general formula (A) by p.

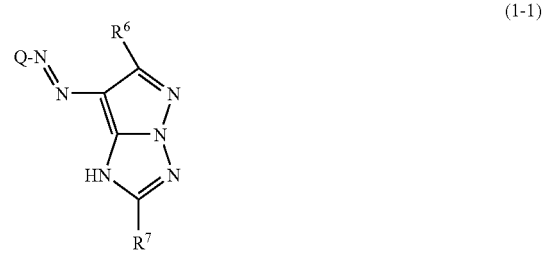
(1-1)

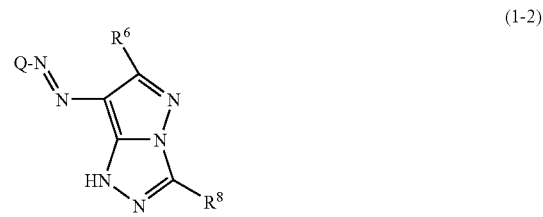
(1-2)

In the general formulae (1-1) and (1-2), Q represents a carbocyclic group or a heterocyclic group. $R^6$ to $R^8$ independently represent a hydrogen atom or a substituent.

[3] An optical information recording medium according to [2], wherein the azo-metal complex dye is represented by the following general formula (2-1).

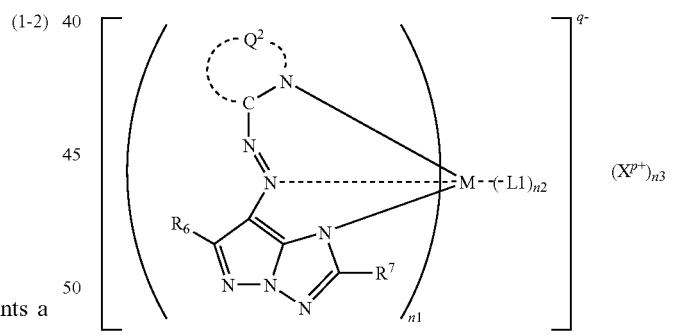
General formula (2-1)

In the general formula (2-1), M represents a metal ion (or a metal oxide ion), and $Q^2$ represents an atomic group forming a heterocycle. L1 represents a ligand. $X^{p+}$ represents a p-valent cation, p represents an integer of 1 to 10, and q represents an integer of 1 to 4. n1 represents 1 or 2, n2 represents an integer of 0 to 3, and n3 represents a value of q/p within a range of $0<n3\leq 4$. $R^6$ and $R^7$ independently represent a hydrogen atom or a substituent.

[4] An optical information recording medium according to [2], wherein the azo-metal complex dye is represented by the following general formula (3-1).

General formula (3-1)

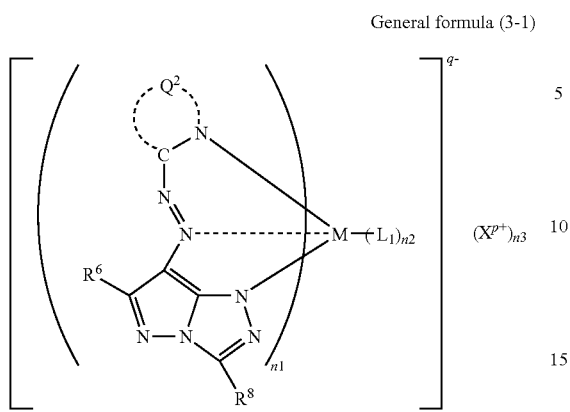

In the general formula (3-1), M represents a metal ion (or a metal oxide ion), and $Q^2$ represents an atomic group forming a heterocycle. L1 represents a ligand. $X^{p+}$ represents a p-valent cation, p represents an integer of 1 to 10, and q represents a number of 1 to 4. n1 represents 1 or 2, n2 represents an integer of 0 to 3, and n3 represents a value of q/p within a range of $0<n3\leq 4$. $R^6$ and $R^8$ independently represent a hydrogen atom or a substituent.

[5] An optical information recording medium according to [1], wherein the azo-metal complex dye contains the metal ion and a divalent azo dye anion provided by eliminating 2 hydrogen atoms from a compound represented by the following general formula (1-1) or (1-2), and the number ratio of the divalent azo dye anion to the metal ion is at most 1/1 in the azo-metal complex dye.

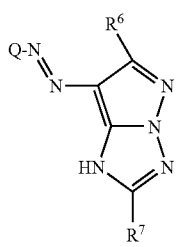
(1-1)

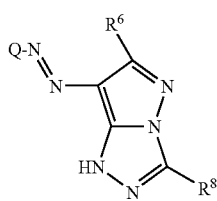
(1-2)

In the general formulae (1-1) and (1-2), Q represents a carbocyclic group or a heterocyclic group. $R^6$ to $R^8$ independently represent a hydrogen atom or a substituent.

[6] An optical information recording medium according to [1], wherein the azo-metal complex dye contains the metal ion and a divalent azo dye anion provided by eliminating 2 hydrogen atoms from a compound represented by the following general formula (1-1) or (1-2), and the number ratio of the divalent azo dye anion to the metal ion is 4/5 in the azo-metal complex dye.

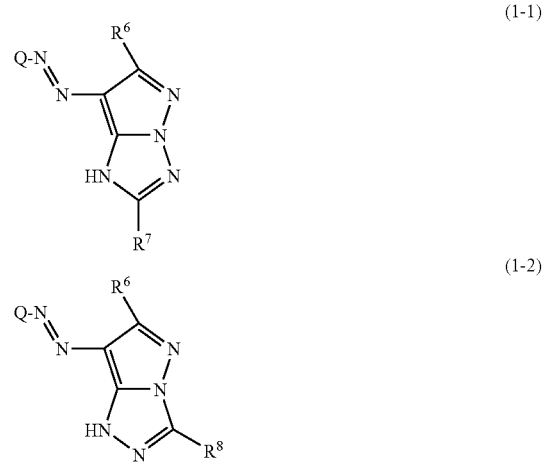

In the general formulae (1-1) and (1-2), Q represents a carbocyclic group or a heterocyclic group. $R^6$ to $R^8$ independently represent a hydrogen atom or a substituent.

[7] An optical information recording medium according to [5], wherein the azo-metal complex dye is represented by the following general formula (B).

$$(L^{2-})_s(L2)_t(M)_u \cdot (Y^{v-})_w \quad \text{General formula (B)}$$

In the general formula (B), $L^{2-}$ represents a divalent azo dye anion provided by eliminating 2 hydrogen atoms from a compound represented by the following general formula (I-1) or (1-2), L2 represents a ligand, M represents a metal ion (or a metal oxide ion), s represents an integer of 1 to 4, t represents an integer of 0 to 14, u represents an integer of 2 to 5, $Y^{v-}$ represents a v-valent anion, v represents an integer of 1 to 10, and w represents a value within a range of $0<w\leq 4$ obtained by dividing the positive charge number in the general formula (B) by v.

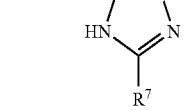
(1-1)

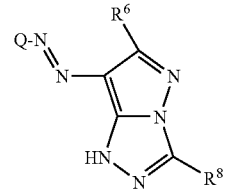
(1-2)

In the general formulae (1-1) and (1-2), Q represents a carbocyclic group or a heterocyclic group. $R^6$ to $R^6$ independently represent a hydrogen atom or a substituent.

[8] An optical information recording medium according to any one of [2] to [4], wherein the $X^{p+}$ is an ammonium cation.

[9] An optical information recording medium according to [1], [5], [6], or [7], wherein the metal ion is a copper ion.

[10] An optical information recording medium according to any one of [1] to [9], wherein a reflection layer and a recording layer are stacked in this order on a pregroove-formed surface of the substrate having pregrooves with a track pitch of 50 to 500 nm.

[11] An azo-metal complex dye according to the present invention, represented by the following general formula (C).

         General formula (C)

In the general formula (C), $L^{2-}$ represents a divalent azo dye anion provided by eliminating 2 hydrogen atoms from a compound represented by the following general formula (1-1) or (1-2), and $(Y^{v-})_w$ represents $(Cl^-)_2$, $(Br^-)_2$, $(I^-)_2$, $(ClO_4^-)_2$, $(PF_6^-)_2$, $(BF_4^-)_2$, $SO_4^{2-}$ or $(CH_3COO^-)_2$.

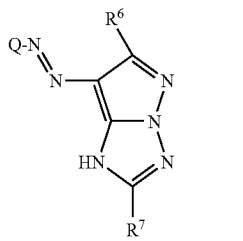

(1-1)

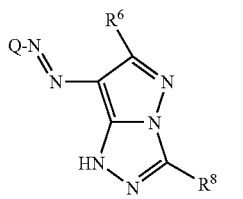

(1-2)

In the general formulae (1-1) and (1-2), Q represents a substituted or unsubstituted pyrazole ring group. $R^6$ to $R^8$ independently represent a substituted or unsubstituted alkyl group or a substituted or unsubstituted aryl group.

As described above, the optical information recording medium of the present invention (particularly the optical information recording medium capable of information recording by irradiation with a laser light having a wavelength of 440 nm or less) contains the azo-metal complex dye of the present invention in the recording layer, and thereby has excellent recording/reproducing properties and remarkably high light fastness.

The azo-metal complex dye of the present invention can be used also for photographic materials, UV absorbers, color filter dyes, color conversion filters, thermal transfer recording materials, inks, and the like.

The above and other objects, features and advantages of the present invention will become more apparent from the following description when taken in conjunction with the accompanying drawings in which a preferred embodiment of the present invention is shown by way of illustrative example.

BEST MODE FOR CARRYING OUT THE INVENTION

Figure 1:
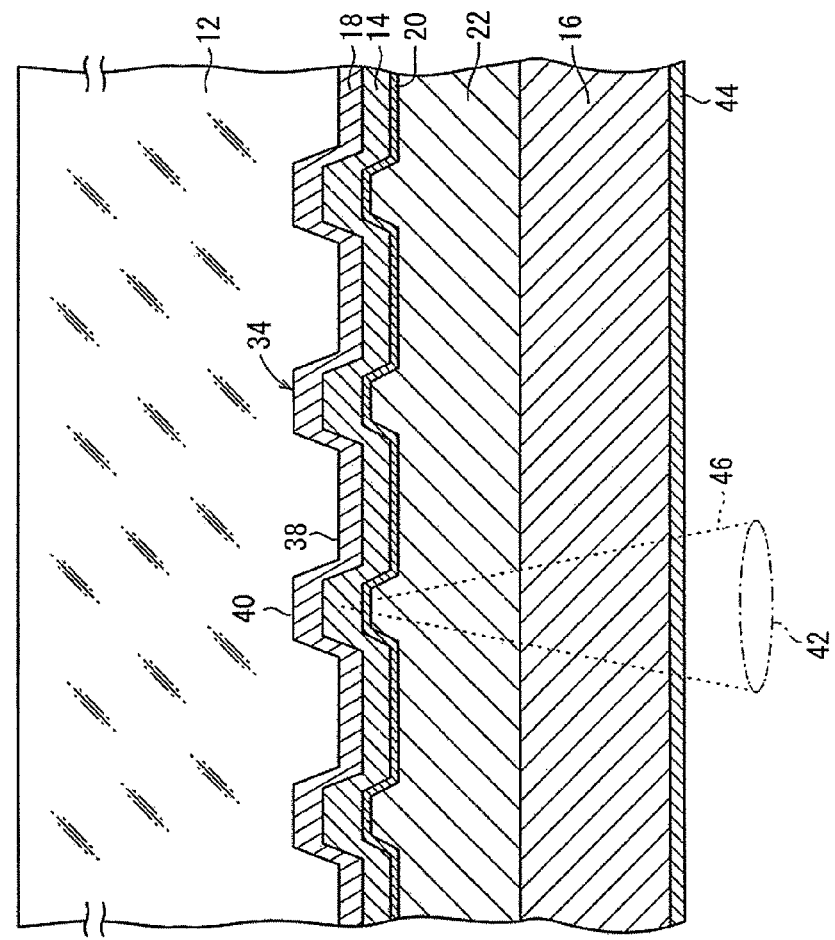
FIG. 1 is a schematic cross-sectional view showing an example of an optical information recording medium according to Embodiment (1).

The optical information recording medium and the azo-metal complex dye of the present invention are described in detail below.

The optical information recording medium of the present invention has at least one recording layer on a substrate, and information can be recorded on the recording layer. It is preferred that the optical information recording medium further has a light reflection layer and a protective layer.

The recording layer in the optical information recording medium of the present invention contains at least one particular azo-metal complex dye.

First the azo-metal complex dye of the present invention is described below. The azo-metal complex dye is prepared by reacting an azo dye represented by the general formula (1-1) or (1-2) with a metal ion under a predetermined condition.

The azo dye represented by the general formula (1-1) or (1-2) has a dissociative hydrogen atom in Q. The dissociative hydrogen atom in Q and the hydrogen atom in the —NH— group marked with asterisk * in the general formula (I-1) or (1-2) are eliminated, and the residue is bonded to the metal ion to generate the azo-metal complex dye. The azo-metal complex dye may contain a component other than the metal ion and the azo dye of the general formula (1-1) or (1-2).

The predetermined condition for reacting the azo dye represented by the general formula (1-1) or (1-2) with the metal ion is that at least a base is contained in the reaction system. The base is not particularly limited as long as the azo-metal complex dye can be synthesized under the presence of the base. Examples of such bases include alkylamines (such as triethylamine, ethylenediamine, morpholine, and pyrazine), arylamines, amidines (such as 1,8-diazabicyclo[5.4.0]undec-7-ene), guanidine, nitrogen-containing aromatic heterocycles (such as pyridine and imidazole), and inorganic bases (such as ammonium acetate, sodium hydrogen carbonate, sodium carbonate, sodium hydroxide, potassium carbonate, potassium hydroxide, and ammonia).

The pKa (the acid dissociation constant) of the dissociative hydrogen atom in Q is preferably in such a range that the dissociative hydrogen atom can be dissociated by the above described base, though not restrictive as long as Q can be in the dissociated state eventually. The pKa is preferably 20 or less, more preferably 15 or less, further preferably 10 or less.

The component other than the metal ion and the azo dye of the general formula (1-1) or (1-2) is not particularly limited, and examples thereof include reaction solvents, bases, azo dyes not represented by the general formula (1-1) or (1-2), and ligands to be hereinafter described.

Examples of the metal ions (or metal ions contained in the metal oxide ions) include ions of Mg, Al, Si, Ca, Sc, Ti, V, Cr, Mn, Fe, Co, Ni, Cu, Zn, Ga, Ge, As, Sr, Y, Zr, Nb, Mo, Tc, Ru, Rh, Pd, Ag, Cd, In, Sn, Sb, Ba, Pr, Eu, Yb, Hf, Ta, W, Re, Os, Ir, Pt, Au, Hg, Tl, Pb, Bi, and Th. Preferred among them are ions of transition metals. The transition metals are elements of Groups IIIa to VIII and Ib of the Periodic Table of Elements, which have an incomplete d-electron shell. The transition metal is not particularly limited, and preferably Mn, Fe, Co, Ni, Cu, Zn, Cr, Ru, Rh, Pd, Ir, Pt, or Re, more preferably Cr, Mn, Fe, Co, Ni, Cu, or Zn, further preferably Mn, Fe, Co, Ni, Cu, or Zn, particularly preferably Fe, Co, Ni, or Cu.

The metal ion is preferably divalent or trivalent. Examples of the divalent or trivalent metal ions include $Mn^{2+}$, $Fe^{2+}$, $Fe^{3+}$, $Co^{2+}$, $Co^{3+}$, $Ni^{2+}$, $Ni^{3+}$, $Cu^{2+}$, $Zn^{2+}$, $Cr^{3+}$, $Ru^{2+}$, $Rh^{3+}$, $Pd^{2+}$, $Ir^{3+}$, $Pt^{2+}$, and $R^+$. Preferred among them are $Mn^{2+}$, $Fe^{2+}$, $Fe^{3+}$, $CO^{2+}$, $CO^{3+}$, $Ni^{2+}$, $Ni^{3+}$, $Cu^{2+}$, and $Zn^{2+}$, more preferred are $Mn^{2+}$, $Fe^{2+}$, $Co^{2+}$, $Co^{3+}$, $Ni^{2+}$, $Cu^{2+}$, and $Zn^{2+}$, and further preferred are $Fe^{2+}$, $Co^{2+}$, $Co^{3+}$, $Ni^{2+}$, $Ni^{3+}$, and $Cu^{2+}$. In the azo-metal complex dye of the present invention, $Cu^{2+}$ is particularly preferred from the viewpoints of the light fastness and the recording/reproducing properties.

In conventional azo-metal complexes for optical information recording media, Ni ions and Co ions have been more widely used than Cu ions from the viewpoint of the light fastness. However, the Cu ions are preferable to the Ni and Co ions in terms of toxicity to the environment and human health. It is especially significant to use low-toxic metal ions such as Cu ions, Zn ions, and Fe ions for expanding the use of the optical information recording media and the azo-metal complex dyes.

The general formulae (1-1) and (1-2) are described below. $R^6$ to $R^8$ independently represent a hydrogen atom or a substituent. Each of $R^6$ to $R^8$ is preferably the substituent in view of increasing the solubility. The substituent of $R^6$ to $R^8$ is not particularly limited, and examples thereof include halogen atoms, alkyl groups including cycloalkyl groups and bicycloalkyl groups, alkenyl groups including cycloalkenyl groups and bicycloalkenyl groups, alkynyl groups, aryl groups, heterocyclic groups, a cyano group, a hydroxyl group, a nitro group, a carboxyl group, alkoxy groups, aryloxy groups, silyloxy groups, heterocyclyloxy groups, acyloxy groups, carbamoyloxy groups, alkoxycarbonyloxy groups, aryloxycarbonyloxy groups, amino groups including anilino groups, acylamino groups, aminocarbonylamino groups, alkoxycarbonylamino groups, aryloxycarbonylamino groups, sulfamoylamino groups, alkyl or aryl sulfonylamino groups, mercapto groups, alkylthio groups, arylthio groups, heterocyclylthio groups, sulfamoyl groups, a sulfo group, alkyl or aryl sulfinyl groups, alkyl or aryl sulfonyl groups, acyl groups, aryloxycarbonyl groups, alkoxycarbonyl groups, carbamoyl groups, aryl or heterocyclyl azo groups, imide groups, phosphino groups, phosphinyl groups, phosphinyloxy groups, phosphinylamino groups, and silyl groups.

More specifically, examples of the substituents of $R^6$ to $R^8$ include halogen atoms such as chlorine, bromine, and iodine atoms; alkyl groups, which may be linear, branched, or cyclic and may be substituted or unsubstituted, including noncyclic alkyl groups (preferably alkyl groups having 1 to 30 carbon atoms, such as methyl, ethyl, n-propyl, isopropyl, t-butyl, n-octyl, eicosyl, 2-chloroethyl, 2-cyanoethyl, and 2-ethylhexyl groups), cycloalkyl groups (preferably substituted or unsubstituted cycloalkyl groups having 3 to 30 carbon atoms, such as cyclohexyl, cyclopentyl and 4-n-dodecylcyclohexyl groups), bicycloalkyl groups (preferably substituted or unsubstituted, monovalent bicycloalkyl groups having 5 to 30 carbon atoms provided by eliminating one hydrogen atom from bicycloalkanes having 5 to 30 carbon atoms, such as bicyclo[1,2,2]heptan-2-yl and bicyclo[2,2,2]octan-3-yl groups), and polycyclic alkyl groups having more cyclic structures such as tricycloalkyl groups, alkyl groups in the flowing substituents (e.g. alkyl groups in alkylthio groups) having the same meanings; alkenyl groups, which may be linear, branched, or cyclic and may be substituted or unsubstituted, including noncyclic alkenyl groups (preferably substituted or unsubstituted alkenyl groups having 2 to 30 carbon atoms, such as vinyl, allyl, prenyl, geranyl, and oleyl groups), cycloalkenyl groups (preferably substituted or unsubstituted, monovalent cycloalkenyl groups having 3 to 30 carbon atoms provided by eliminating one hydrogen atom from cycloalkenes having 3 to 30 carbon atoms, such as 2-cyclopenten-1-yl and 2-cyclohexen-1-yl groups), and bicycloalkenyl groups (preferably substituted or unsubstituted, monovalent bicycloalkenyl groups having 5 to 30 carbon atoms provided by eliminating one hydrogen atom from bicycloalkenes having a double bond, such as bicyclo[2,2,1]hept-2-ene-1-yl and bicyclo[2,2,2]oct-2-ene-4-yl groups); alkynyl groups (preferably substituted or unsubstituted alkynyl groups having 2 to 30 carbon atoms, such as ethynyl, propargyl, and trimethylsilylethynyl groups); aryl groups (preferably substituted or unsubstituted aryl groups having 6 to 30 carbon atoms, such as phenyl, p-tolyl, naphthyl, m-chlorophenyl, and o-hexadecanoylaminophenyl groups); heterocyclic groups (preferably monovalent groups provided by eliminating one hydrogen atom form 5- or 6-membered, substituted or unsubstituted, aromatic or nonaromatic, heterocyclic compounds, more preferably 5- or 6-membered aromatic heterocyclic groups having 3 to 30 carbon atoms, such as 2-furyl, 2-thienyl, 2-pyrimidinyl, and 2-benzothiazolyl groups); a cyano group; a hydroxyl group; a nitro group; a carboxyl group; alkoxy groups (preferably substituted or unsubstituted alkoxy groups having 1 to 30 carbon atoms, such as methoxy, ethoxy, isopropoxy, t-butoxy, n-octyloxy, and 2-methoxyethoxy groups); aryloxy groups (preferably substituted or unsubstituted aryloxy groups having 6 to 30 carbon atoms, such as phenoxy, 2-methylphenoxy, 4-t-butylphenoxy, 3-nitrophenoxy, and 2-tetradecanoylaminophenoxy groups); silyloxy groups (preferably silyloxy groups having 3 to 20 carbon atoms, such as trimethylsilyloxy and t-butyldimethylsilyloxy groups); heterocyclyloxy groups (preferably substituted or unsubstituted heterocyclyloxy groups having 2 to 30 carbon atoms, such as 1-phenyltetrazole-5-oxy and 2-tetrahydropyranyloxy groups); acyloxy groups (preferably a formyloxy group, substituted or unsubstituted alkylcarbonyloxy groups having 2 to 30 carbon atoms, and substituted or unsubstituted arylcarbonyloxy groups having 6 to 30 carbon atoms, such as formyloxy, acetyloxy, pivaloyloxy, stearoyloxy, benzoyloxy, and p-methoxyphenylcarbonyloxy groups); carbamoyloxy groups (preferably substituted or unsubstituted carbamoyloxy groups having 1 to 30 carbon atoms, such as N,N-dimethylcarbamoyloxy, N,N-diethylcarbamoyloxy, morpholinocarbonyloxy, N,N-di-n-octylaminocarbonyloxy, and N-n-octylcarbamoyloxy groups); alkoxycarbonyloxy groups (preferably substituted or unsubstituted alkoxycarbonyloxy groups having 2 to 30 carbon atoms, such as methoxycarbonyloxy, ethoxycarbonyloxy, t-butoxycarbonyloxy, and n-octylcarbonyloxy groups); aryloxycarbonyloxy groups (preferably substituted or unsubstituted aryloxycarbonyloxy groups having 7 to 30 carbon atoms, such as phenoxycarbonyloxy, p-methoxyphenoxycarbonyloxy, and p-n-hexadecyloxyphenoxycarbonyloxy groups); amino groups (preferably an amino group, substituted or unsubstituted alkylamino groups having 1 to 30 carbon atoms, and substituted or unsubstituted anilino groups having 6 to 30 carbon atoms, such as amino, methylamino, dimethylamino, anilino, N-methylanilino, and diphenylamino groups); acylamino groups (preferably a formylamino group, substituted or unsubstituted alkylcarbonylamino groups having 1 to 30 carbon atoms, and substituted or unsubstituted arylcarbonylamino groups having 6 to 30 carbon atoms, such as formylamino, acetylamino, pivaloylamino, lauroylamino, benzoylamino, and 3,4,5-tri-n-octyloxyphenylcarbonylamino groups); aminocarbonylamino groups (preferably substituted or unsubstituted aminocarbonylamino groups having 1 to 30 carbon atoms, such as carbamoylamino, N,N-dimethylaminocarbonylamino, N,N-diethylaminocarbonylamino, and morpholinocarbonylamino groups); alkoxycarbonylamino groups (preferably substituted or unsubstituted alkoxycarbonylamino groups having 2 to 30 carbon atoms, such as methoxycarbonylamino, ethoxycarbonylamino, t-butoxycarbonylamino, n-octadecyloxycarbonylamino, and N-methyl-methoxycarbonylamino groups); aryloxycarbonylamino groups (preferably substituted or unsubstituted aryloxycarbonylamino groups having 7 to 30 carbon atoms, such as phenoxycarbonylamino, p-chlorophenoxycarbonylamino, and m-n-octyloxyphenoxycarbonylamino groups); sulfamoylamino groups (preferably substituted or unsubstituted sulfamoylamino groups having 0 to 30 carbon atoms, such as sulfamoylamino, N,N-dimethylaminosulfonylamino, and N-n-octylaminosulfonylamino groups); alkyl or aryl sulfonylamino groups (preferably substituted or unsubstituted alkylsulfonylamino groups having 1 to 30 carbon atoms and substituted or unsubstituted arylsulfonylamino groups having 6 to 30 carbon atoms, such as methylsulfonylamino, butylsulfonylamino, phenylsulfonylamino, 2,3,5-trichlorophenylsulfonylamino, and p-methylphenylsulfonylamino groups); a mercapto group; alkylthio groups (preferably substituted or unsubstituted alkylthio groups having 1 to 30 carbon atoms, such as methylthio, ethylthio, and n-hexadecylthio groups); arylthio groups (preferably substituted or unsubstituted arylthio groups having 6 to 30 carbon atoms, such as phenylthio, p-chlorophenylthio, and m-methoxyphenylthio groups); heterocyclylthio groups (preferably substituted or unsubstituted heterocyclylthio groups having 2 to 30 carbon atoms, such as 2-benzothiazolylthio and 1-phenyltetrazol-5-ylthio groups); sulfamoyl groups (preferably substituted or unsubstituted sulfamoyl groups having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl) sulfamoyl groups); a sulfo group; alkyl or aryl sulfinyl groups (preferably substituted or unsubstituted alkylsulfinyl groups having 1 to 30 carbon atoms and substituted or unsubstituted arylsulfinyl groups having 6 to 30 carbon atoms, such as methylsulfinyl, ethylsulfinyl, phenylsulfinyl, and p-methylphenylsulfinyl groups); alkyl or aryl sulfonyl groups (preferably substituted or unsubstituted alkylsulfonyl groups having 1 to 30 carbon atoms and substituted or unsubstituted arylsulfonyl groups having 6 to 30 carbon atoms, such as methylsulfonyl, ethylsulfonyl, phenylsulfonyl, and p-methylphenylsulfonyl groups); acyl groups (preferably a formyl group, substituted or unsubstituted alkylcarbonyl groups having 2 to 30 carbon atoms, substituted or unsubstituted arylcarbonyl groups having 7 to 30 carbon atoms, and substituted or unsubstituted heterocyclylcarbonyl groups having 4 to 30 carbon atoms and a heterocycle containing a carbon atom bonded to a carbonyl group, such as acetyl, pivaloyl, 2-chloroacetyl, stearoyl, benzoyl, p-n-octyloxyphenylcarbonyl, 2-pyridylcarbonyl, and 2-furylcarbonyl groups); aryloxycarbonyl groups (preferably substituted or unsubstituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl groups); alkoxycarbonyl groups (preferably substituted or unsubstituted alkoxycarbonyl groups having 2 to 30 carbon atoms, such as methoxycarbonyl, ethoxycarbonyl, t-butoxycarbonyl, and n-octadecyloxycarbonyl groups); carbamoyl groups (preferably substituted or unsubstituted carbamoyl groups having 1 to 30 carbon atoms, such as carbamoyl, N-methylcarbamoyl, N,N-dimethylcarbamoyl, N,N-di-n-octylcarbamoyl, and N-(methylsulfonyl)carbamoyl groups); aryl or heterocyclyl azo groups (preferably substituted or unsubstituted arylazo groups having 6 to 30 carbon atoms and substituted or unsubstituted heterocyclylazo groups having 3 to 30 carbon atoms, such as phenylazo, p-chlorophenylazo, and 5-ethylthio-1,3,4-thiadiazol-2-yl azo groups); imide groups (preferably N-succinimide and N-phthalimide groups); phosphino groups (preferably substituted or unsubstituted phosphino groups having 2 to 30 carbon atoms, such as dimethylphosphino, diphenylphosphino, and methylphenoxyphosphino groups); phosphinyl groups (preferably substituted or unsubstituted phosphinyl groups having 2 to 30 carbon atoms, such as phosphinyl, dioctyloxyphosphinyl, and diethoxyphosphinyl groups); phosphinyloxy groups (preferably substituted or unsubstituted phosphinyloxy groups having 2 to 30 carbon atoms, such as diphenoxyphosphinyloxy and dioctyloxyphosphinyloxy groups); phosphinylamino groups (preferably substituted or unsubstituted phosphinylamino groups having 2 to 30 carbon atoms, such as dimethoxyphosphinylamino and dimethylaminophosphinylamino groups); and silyl groups (preferably substituted or unsubstituted silyl groups having 3 to 30 carbon atoms, such as trimethylsilyl, t-butyldimethylsilyl, and phenyldimethylsilyl groups).

A hydrogen atom in the above functional groups may be further substituted by the functional groups. Examples of such substituents include alkylcarbonylaminosulfonyl groups, arylcarbonylaminosulfonyl groups, alkylsulfonylaminocarbonyl groups, and arylsulfonylaminocarbonyl groups. Specific examples thereof include a methylsulfonylaminocarbonyl group, a p-methylphenylsulfonylaminocarbonyl group, an acetylaminosulfonyl group, and a benzoylaminosulfonyl group.

$R^6$ is preferably a substituted or unsubstituted alkyl group having 1 to 10 carbon atoms, a substituted or unsubstituted aryl group having 6 to 20 carbon atoms, a substituted or unsubstituted alkoxy group having 1 to 10 carbon atoms, a substituted or unsubstituted aryloxy group having 6 to 20 carbon atoms, a substituted or unsubstituted acyl group having 2 to 10 carbon atoms, a substituted or unsubstituted alkoxycarbonyl group having 2 to 10 carbon atoms, or a substituted or unsubstituted alkylsulfonyl group having 1 to 10 carbon atoms, more preferably a substituted or unsubstituted alkyl group having 1 to 8 carbon atoms or a substituted or unsubstituted aryl group having 6 to 15 carbon atoms, further preferably a substituted or unsubstituted alkyl group having 1 to 6 carbon atoms. The alkyl group is preferably a branched alkyl group having 3 to 6 carbon atoms, more preferably a tertiary alkyl group having 4 to 6 carbon atoms.

Each of $R^7$ and $R^8$ is preferably a substituent. The substituent is preferably a substituted or unsubstituted alkyl group having 1 to 10 carbon atoms or a substituted or unsubstituted aryl group having 6 to 20 carbon atoms, more preferably a substituted or unsubstituted alkyl group having 1 to 6 carbon atoms.

Although the azo dye represented by the general formula (1-1) or (1-2) according to this embodiment is shown above in the azo form in the azo-hydrazone tautomeric equilibrium, the azo dye may be in the hydrazone form. In the present invention, the dye in the hydrazone form is considered to be equivalent to that in the azo form.

Q represents a carbocyclic group or a heterocyclic group. Q has a ring or substituent containing an atom capable of forming a covalent bond with the metal ion. When Q has the substituent containing the atom capable of bonding to the metal ion, one hydrogen atom in the substituent is removed to form the covalent bond with the metal ion. Examples of such substituents that release a hydrogen atom to form the covalent bond with the metal ion include a hydroxyl group, a thiol group, amino groups, a carboxyl group, and a sulfonic acid group.

When Q has the substituent containing the atom capable of covalent-bonding to the metal ion, preferred examples of the substituents include a hydroxyl group; amino groups (preferably an amino group, substituted or unsubstituted alkylamino groups having 1 to 30 carbon atoms, and substituted or unsubstituted anilino groups having 6 to 30 carbon atoms, such as amino, methylamino, dimethylamino, anilino, N-methylanilino, and diphenylamino groups); acylamino groups (preferably a formylamino group, substituted or unsubstituted alkylcarbonylamino groups having 1 to 30 carbon atoms, and substituted or unsubstituted arylcarbonylamino groups having 6 to 30 carbon atoms, such as formylamino, acetylamino, pivaloylamino, lauroylamino, benzoylamino, and 3,4,5-tri-n-octyloxyphenylcarbonylamino groups); aminocarbonylamino groups (preferably substituted or unsubstituted aminocarbonylamino groups having 1 to 30 carbon atoms, such as carbamoylamino, N,N-dimethylaminocarbonylamino, N,N-diethylaminocarbonylamino, and morpholinocarbonylamino groups); alkoxycarbonylamino groups (preferably substituted or unsubstituted alkoxycarbonylamino groups having 2 to 30 carbon atoms, such as methoxycarbonylamino, ethoxycarbonylamino, t-butoxycarbonylamino, n-octadecyloxycarbonylamino, and N-methyl-methoxycarbonylamino groups); aryloxycarbonylamino groups (preferably substituted or unsubstituted aryloxycarbonylamino groups having 7 to 30 carbon atoms, such as phenoxycarbonylamino, p-chlorophenoxycarbonylamino, and m-n-octyloxyphenoxycarbonylamino groups); sulfamoylamino groups (preferably substituted or unsubstituted sulfamoylamino groups having 0 to 30 carbon atoms, such as sulfamoylamino, N,N-dimethylaminosulfonylamino, and N-n-octylaminosulfonylamino groups); and alkyl or aryl sulfonylamino groups (preferably substituted or unsubstituted alkylsulfonylamino groups having 1 to 30 carbon atoms and substituted or unsubstituted arylsulfonylamino groups having 6 to 30 carbon atoms, such as methylsulfonylamino, butylsulfonylamino, phenylsulfonylamino, 2,3,5-trichlorophenylsulfonylamino, and p-methylphenylsulfonylamino groups). When the substituent forming the covalent bond with the metal ion is an amino group having a substituent, the amino group is preferably a substituted or unsubstituted anilino group having 6 to 30 carbon atoms, a substituted or unsubstituted acylamino group having 2 to 30 carbon atoms, a substituted or unsubstituted arylcarbonylamino group having 6 to 30 carbon atoms, a substituted or unsubstituted aminocarbonylamino group having 1 to 30 carbon atoms, a substituted or unsubstituted alkoxycarbonylamino group having 2 to 30 carbon atoms, a substituted or unsubstituted aryloxycarbonylamino group having 7 to 30 carbon atoms, a substituted or unsubstituted sulfamoylamino group having 0 to 30 carbon atoms, a substituted or unsubstituted alkylsulfonylamino group having 1 to 30 carbon atoms, or a substituted or unsubstituted arylsulfonylamino group having 6 to 30 carbon atoms, more preferably a substituted or unsubstituted acylamino group having 2 to 30 carbon atoms, a substituted or unsubstituted arylcarbonylamino group having 6 to 30 carbon atoms, a substituted or unsubstituted aminocarbonylamino group having 1 to 30 carbon atoms, a substituted or unsubstituted alkoxycarbonylamino group having 2 to 30 carbon atoms, a substituted or unsubstituted sulfamoylamino group having 0 to 30 carbon atoms, or a substituted or unsubstituted alkylsulfonylamino group having 1 to 30 carbon atoms, further preferably a substituted or unsubstituted acylamino group having 2 to 30 carbon atoms, a substituted or unsubstituted alkoxycarbonylamino group having 2 to 30 carbon atoms, or a substituted or unsubstituted alkylsulfonylamino group having 1 to 30 carbon atoms, particularly preferably a substituted or unsubstituted acylamino group having 2 to 30 carbon atoms, or a substituted or unsubstituted alkoxycarbonylamino group having 2 to 30 carbon atoms.

The carbocyclic group of Q is preferably a phenyl group. Q may have a further substituent in addition to the substituent containing the atom capable of forming the bond with the metal ion. It is preferred that Q has the further substituent from the viewpoint of increasing the solubility. The further substituent is not particularly limited, and is preferably a group other than a hydroxyl group, alkyloxy groups, aryloxy groups, a thiol group, alkylthio groups, arylthio groups, amino groups, alkylamino groups, and anilino groups. The further substituent is preferably a halogen atom, a nitro group, a cyano group, a substituted or unsubstituted alkyl group having 1 to 10 carbon atoms, a substituted or unsubstituted aryl group having 6 to 20 carbon atoms, a substituted or unsubstituted acyl group having 2 to 10 carbon atoms, a substituted or unsubstituted alkoxycarbonyl group having 2 to 10 carbon atoms, a substituted or unsubstituted aryloxycarbonyl group having 7 to 10 carbon atoms, a substituted or unsubstituted alkylsulfonyl group having 1 to 10 carbon atoms, a substituted or unsubstituted arylsulfonyl group having 6 to 10 carbon atoms, or a substituted or unsubstituted alkoxysulfonyl group having 1 to 10 carbon atoms, more preferably a cyano group, a substituted or unsubstituted alkyl group having 1 to 10 carbon atoms, a substituted or unsubstituted aryl group having 6 to 20 carbon atoms, a substituted or unsubstituted acyl group having 2 to 10 carbon atoms, a substituted or unsubstituted alkoxycarbonyl group having 2 to 10 carbon atoms, a substituted or unsubstituted alkylsulfonyl group having 1 to 10 carbon atoms, or a substituted or unsubstituted arylsulfonyl group having 6 to 10 carbon atoms, further preferably a substituted or unsubstituted alkyl group having 1 to 10 carbon atoms, a substituted or unsubstituted acyl group having 2 to 10 carbon atoms, a substituted or unsubstituted alkoxycarbonyl group having 2 to 10 carbon atoms, or a substituted or unsubstituted alkylsulfonyl group having 1 to 10 carbon atoms.

In a case where Q is a heterocyclic group, Q has the ring or substituent containing the atom capable of forming the covalent bond with the metal ion.

When Q has the ring capable of forming the covalent bond with the metal ion, examples of such rings include those represented by the formulae (q-1) to (q-4) to be hereinafter described for the general formula (2-1).

When Q has the substituent containing the atom capable of forming the covalent bond with the metal ion, the substituent forming the covalent bond with the metal ion may be the same as described above regardless of whether Q is a carbocyclic group or a heterocyclic group.

When Q is a heterocyclic group having the substituent containing the atom capable of forming the covalent bond with the metal ion, the heterocycle of Q is not particularly limited, and may be a pyrazole ring, a pyrrole ring, a furan ring, a thiophene ring, an imidazole ring, a thiazole ring, an oxazole ring, an isothiazole ring, an isoxazole ring, a pyridine ring, a pyrazine ring, a pyrimidine ring, a pyridazine ring, a triazine ring, or the like. The heterocyclic group preferably contains a pyrazole ring, an isothiazole ring, an isoxazole ring, a pyridine ring, a pyrazine ring, a pyrimidine ring, a pyridazine ring, or a triazine ring, and more preferably contains a pyrazole ring, a pyridine ring, or a triazine ring.

Q preferably has a substituent. The substituent is not particularly limited, and examples thereof are the same as those of $R^6$ to $R^8$.

Q preferably has a nitrogen-containing heterocycle formed by $Q^2$ to be hereinafter described.

Among the general formulae (1-1) and (1-2), the general formula (1-1) is preferred from the viewpoint of light fastness.

Specific examples of the azo dyes represented by the general formula (1-1) are illustrated below without intention of restricting the scope of the present invention.
(A-1)
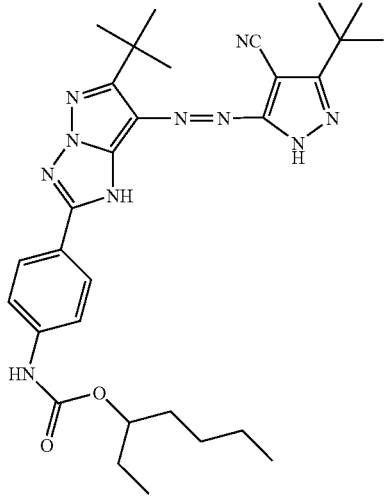
(A-2)
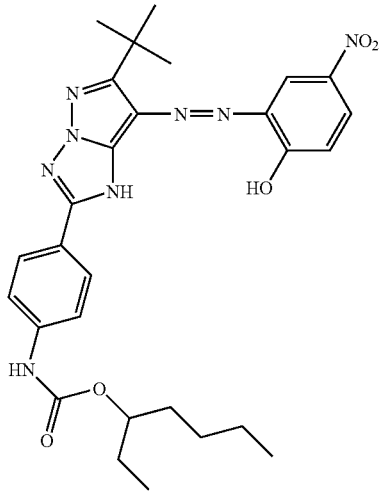
(A-3)
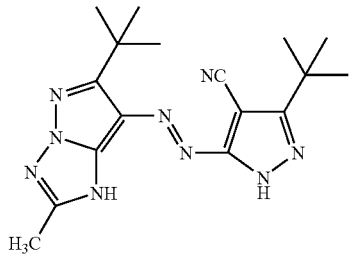
(A-4)
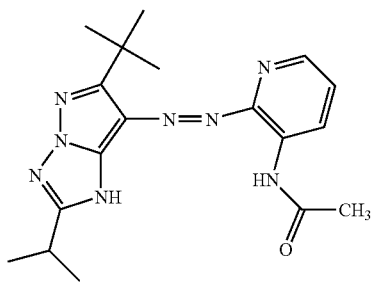
(A-5)
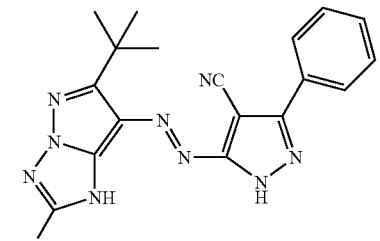
(A-6)
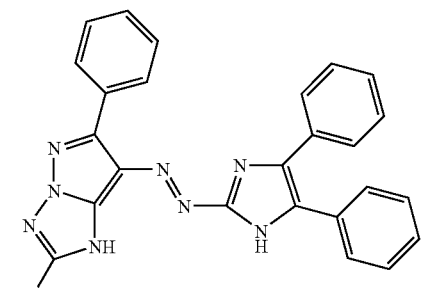
(A-7)
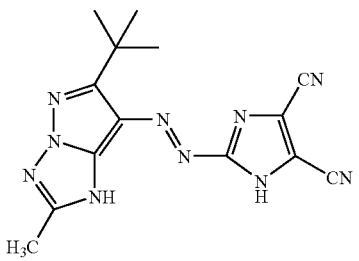
(A-8)
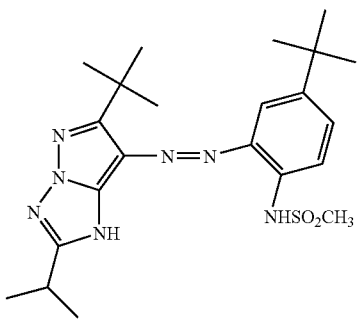
(A-9)
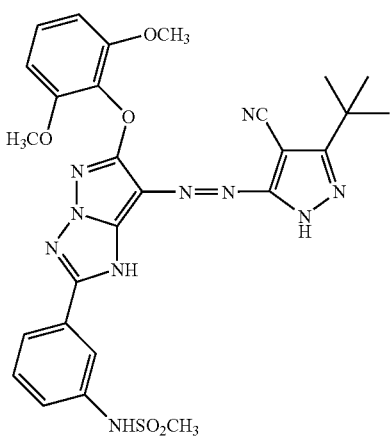

Specific examples of the azo dyes represented by the general formula (1-2) are illustrated below without intention of restricting the scope of the present invention.

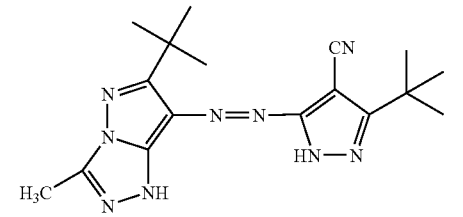

(A-10)

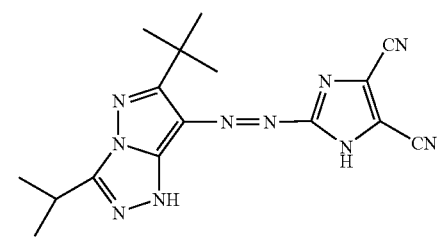

(A-11)

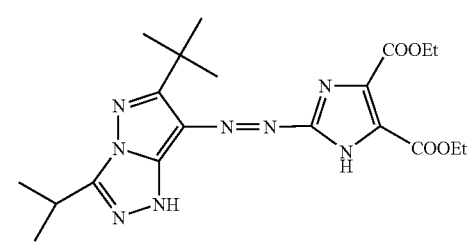

(A-12)

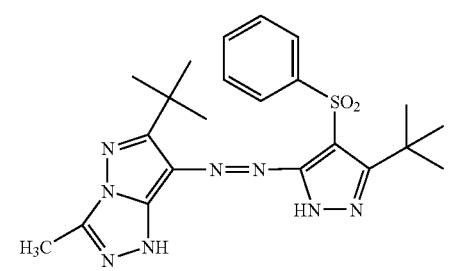

(A-13)

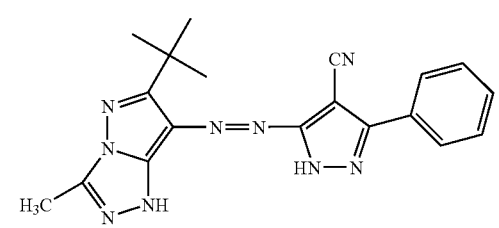

(A-14)

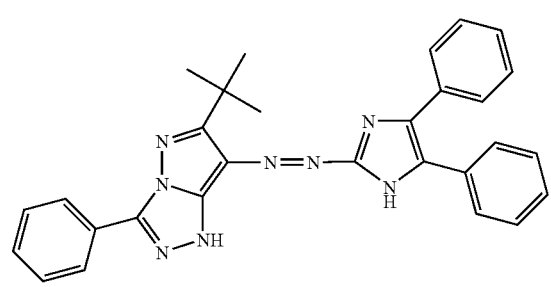

(A-15)

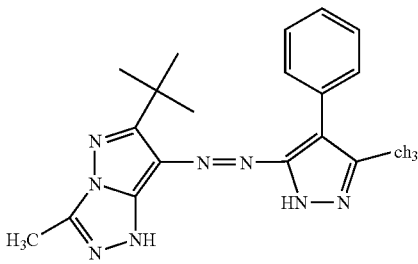

(A-16)

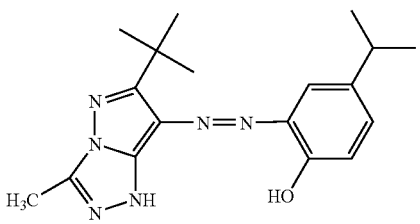

(A-17)

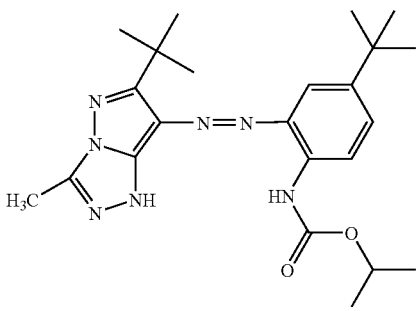

(A-18)

The azo-metal complex dye is preferably represented by the general formula (A) or (B), and more preferably represented by the general formula (B) in view of recording properties.

The general formula (A) is described in detail below.

When the metal ion is trivalent, the azo-metal complex dye of the present invention is likely to have a coordination structure represented by the general formula (A). In the general formula (A), M represents a metal ion or a metal oxide ion, and is preferably $Co^{3+}$, $Ni^{3+}$, or $Fe^{3+}$, more preferably $Co^{3+}$ or $Ni^{3+}$, further preferably $Co^{3+}$.

L' represents a ligand. The ligand means an atom or an atomic group that is bonded to the metal ion. The ligand may be selected from the preferred examples to be hereinafter described and those described in H. Yersin, "Photochemistry and Photophysics of Coordination Compounds", Springer-Verlag, 1987, Akio Yamamoto, "Yuki Kinzoku Kagaku Kiso to Oyo (Organometallic Chemistry, Foundation and Application)", Shokabo Publishing Co., Ltd., 1982, and the like. Specific examples of the ligands are described below.

In L', an atom coordinating to M is preferably a nitrogen atom, an oxygen atom, a sulfur atom, a phosphorus atom, or a halogen atom, more preferably a nitrogen atom, an oxygen atom, or a halogen atom, further preferably a nitrogen atom or an oxygen atom, particularly preferably a nitrogen atom.

When L' is coordinated to M, the bond formed between M and L' may be a covalent bond (a bond) or a coordinate bond. Thus, L' may be an anionic ligand or a neutral ligand.

The ligand of L' having a nitrogen atom coordinating to M is not particularly limited, and examples thereof include nitrogen-containing, aromatic heterocycle ligands such as pyridine ligands, pyrazine ligands, pyrimidine ligands, pyridazine ligands, triazine ligands, triazole ligands, oxazole ligands, pyrrole ligands, imidazole ligands, pyrazole ligands, triazole ligands, oxadiazole ligands, thiadiazole ligands, condensed ligands thereof (e.g. quinoline ligands, benzoxazole ligands, benzimidazole ligands), and tautomers thereof; amine ligands such as ammonia, methylamine, dimethylamine, diethylamine, dibenzylamine, triethylamine, piperidine, piperazine, morpholine, and arylamines; aniline ligands such as aniline, N-methylaniline, N,N-dimethylaniline, N,N-diethylaniline, diphenylamine, N-acylanilines, and N-alkylsulfonylanilines; imine ligands; nitrile ligands such as an acetonitrile ligand; isonitrile ligands such as a t-butylisonitrile ligand; and amide ligands such as a dimethylformamide ligand and a dimethylacetamide ligand. These ligands may have a substituent.

The ligand of L' having an oxygen atom coordinating to M is not particularly limited, and examples thereof include alcohol ligands, preferably having 1 to 30 carbon atoms, more preferably having 1 to 20 carbon atoms, particularly preferably having 1 to 10 carbon atoms, such as monovalent anion ligands provided by eliminating a proton from methanol, ethanol, butanol, 2-ethylhexanol, or the like; aryloxy ligands, preferably having 6 to 30 carbon atoms, more preferably having 6 to 20 carbon atoms, particularly preferably having 6 to 12 carbon atoms, such as monovalent anion ligands provided by eliminating a proton from phenol, 1-naphthol, 2-naphthol, or the like; diketone ligands such as an acetylacetone ligand; silyloxy ligands, preferably having 3 to 40 carbon atoms, more preferably having 3 to 30 carbon atoms, particularly preferably having 3 to 24 carbon atoms, such as a trimethylsilyloxy ligand and a triphenylsilyloxy ligand; ether ligands including cyclic ether ligands; carboxylic acid ligands; sulfonic acid ligands; aqua ligands; and $O_2$ ligands. These ligands may have a substituent.

The ligand of L' having a sulfur atom coordinating to M is not particularly limited, and examples thereof include alkylthiol ligands, preferably having 1 to 30 carbon atoms, more preferably having 1 to 20 carbon atoms, particularly preferably having 1 to 12 carbon atoms, such as monovalent anion ligands provided by eliminating a proton from butanethiol or the like; arylthiol ligands, preferably having 6 to 30 carbon atoms, more preferably having 6 to 20 carbon atoms, particularly preferably having 6 to 12 carbon atoms, such as thiophenol; and thioether ligands. These ligands may have a substituent.

The ligand of L' having a phosphorus atom coordinating to M is not particularly limited, and examples thereof include alkylphosphine ligands, preferably having 2 to 30 carbon atoms, more preferably having 2 to 20 carbon atoms, particularly preferably having 2 to 10 carbon atoms, such as methylphosphine, dimethylphosphine, diethylphosphine, and dibenzylphosphine; and arylphosphine ligands, preferably having 3 to 30 carbon atoms, more preferably having 4 to 20 carbon atoms, particularly preferably having 5 to 10 carbon atoms, such as phenylphosphine, diphenylphosphine, and pyridylphosphine. These ligands may have a substituent.

The ligand of L' coordinating to M may be a halogen ligand such as a chlorine ligand, a fluorine ligand, a bromine ligand, or an iodine ligand.

n is an integer of 1 to 4, preferably 1 or 2. When n is 1, L' is the above described anionic ligand, and m is an integer of 1 to 3.

m is an integer of 0 to 3, preferably an integer of 0 to 2, more preferably 0 or 1.

r is 1 or 2, preferably 1.

k' is a value within the range of $0<k'\leq 4$ obtained by dividing the negative charge number in the general formula (A) by p.

p is an integer of 1 to 10, preferably an integer of 1 to 4, more preferably an integer of 1 to 3, further preferably 1 or 2.

In the general formula (A), $X^{p+}$ represents a p-valent cation. Examples of the cations of $X^{p+}$ include ammonium cations, alkaline metal ions, and alkaline earth metal ions such as $Mg^{2+}$, and the ammonium cations include ammonium cations represented by the following general formula (X) and di- or more-valent ammonium cations represented by the following general formula (XX).

It is preferred that the cation is an ammonium cation represented by the general formula (X) or (XX) from the viewpoint of solubility in coating liquid solvents.

General formula (X)

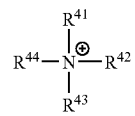

The general formula (X) is described below. $R^{41}$ to $R^{44}$ independently represent a hydrogen atom, an alkyl group, or an aryl group. $R^{41}$ to $R^{44}$ may be connected to each other by a linking group.

More specifically, $R^{41}$ to $R^{44}$ may be selected respectively from alkyl groups, which may be linear, branched, or cyclic and may be substituted or unsubstituted, including noncyclic alkyl groups (preferably alkyl groups having 1 to 30 carbon atoms, such as methyl, ethyl, n-propyl, isopropyl, t-butyl, n-octyl, eicosyl, 2-chloroethyl, 2-cyanoethyl, and 2-ethylhexyl groups), cycloalkyl groups (preferably substituted or unsubstituted cycloalkyl groups having 3 to 30 carbon atoms, such as cyclohexyl, cyclopentyl, and 4-n-dodecylcyclohexyl groups), bicycloalkyl groups (preferably substituted or unsubstituted, monovalent bicycloalkyl groups having 5 to 30 carbon atoms provided by eliminating one hydrogen atom from bicycloalkanes having 5 to 30 carbon atoms, such as bicyclo[1,2,2]heptan-2-yl and bicyclo[2,2,2]octan-3-yl groups), and polycyclic alkyl groups having more cyclic structures such as tricycloalkyl groups, alkyl groups in the flowing substituents (e.g. alkyl groups in alkylthio groups) having the same meanings; and aryl groups (preferably substituted or unsubstituted aryl groups having 6 to 30 carbon atoms, such as phenyl, p-tolyl, naphtyl, m-chlorophenyl, and o-hexadecanoylaminophenyl groups). These groups may further have a substituent.

It is preferred that at least one of $R^{41}$ to $R^{44}$ is a substituted or unsubstituted alkyl group having 1 to 10 carbon atoms or a substituted or unsubstituted aryl group having 6 to 10 carbon atoms.

General formula (XX)

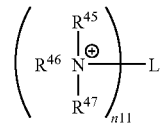

The general formula (XX) is described below. $R^{45}$ to $R^{47}$ independently represent a hydrogen atom, an alkyl group, or an aryl group. n11 represents an integer of 2 to 10. A plurality of $R^{45}$'s, $R^{46}$'s, $R^{47}$'s may be the same or different ones respectively. L represents an alkyl or aryl linking group, which may contain —O— or —S—. $R^{45}$ to $R^{47}$ may be connected to each other by a linking group. $R^{45}$ to, $R^{47}$ and L may further have a substituent.

It is preferred that at least one of $R^{45}$ to $R^{47}$ is a substituted or unsubstituted alkyl group having 1 to 10 carbon atoms or a substituted or unsubstituted aryl group having 6 to 10 carbon atoms.

n11 is preferably an integer of 2 to 8, more preferably an integer of 2 to 4, further preferably 2 or 3, particularly preferably 2.

L is preferably a substituted or unsubstituted alkyl linking group having 1 to 10 carbon atoms, more preferably a substituted or unsubstituted alkyl linking group having 1 to 5 carbon atoms, further preferably a substituted or unsubstituted alkyl linking group having 1 to 3 carbon atoms.

Specific examples of the organic cations are illustrated below without intention of restricting the scope of the present invention.

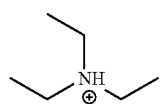 (X-1)

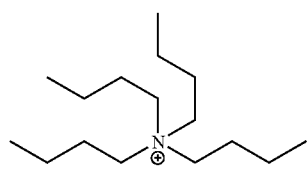 (X-2)

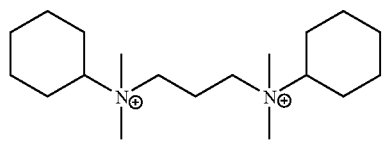 (X-3)

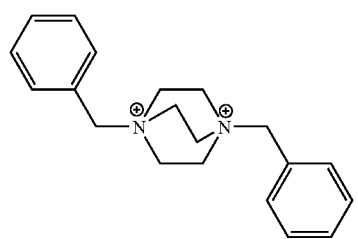 (X-4)

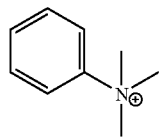 (X-5)

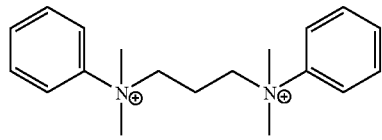 (X-6)

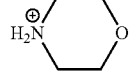 (X-7)

-continued

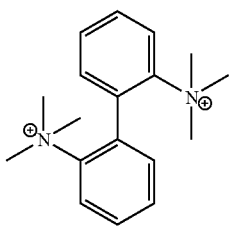 (X-8)

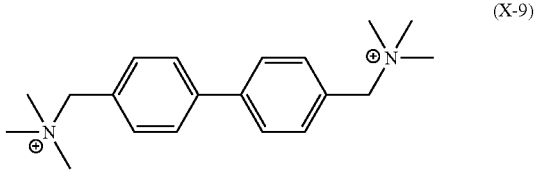 (X-9)

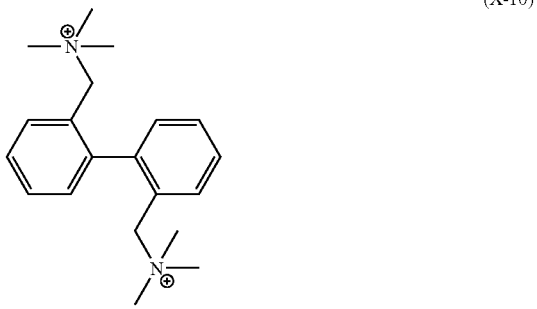 (X-10)

 (X-11)

 (X-12)

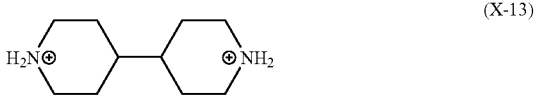 (X-13)

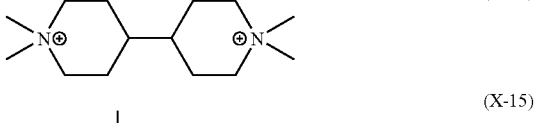 (X-14)

 (X-15)

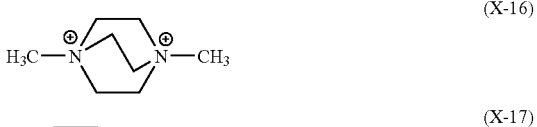 (X-16)

 (X-17)

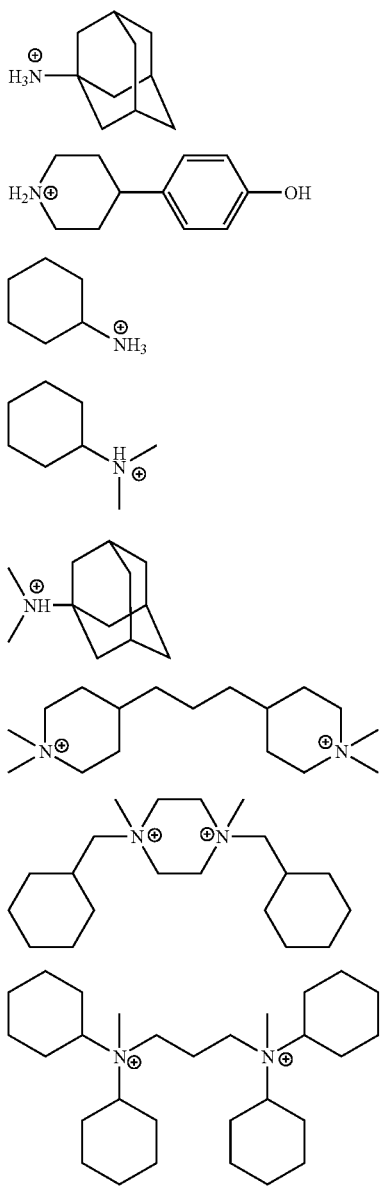

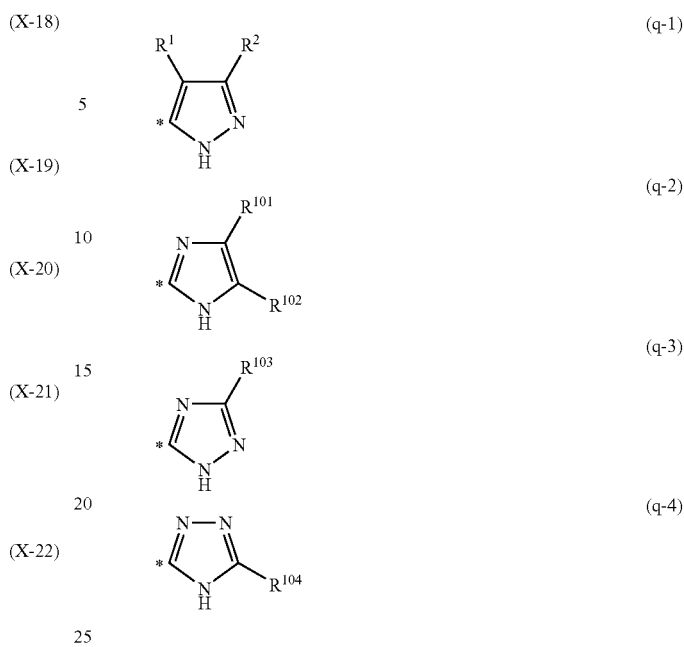

In the structural formulae (q-1) to (q-4), each asterisk * represents a position at which the heterocycle is bonded to the —N=N— group, and $R^1$, $R^2$, and $R^{101}$ to $R^{104}$ independently represent a hydrogen atom or a substituent.

It is preferred that each of $R^1$, $R^2$ to $R^{104}$ be a substituent from the viewpoint of improving the solubility. Examples of the substituents may be the same as those of $R^6$ to $R^8$.

$R^1$ is preferably a substituted or unsubstituted aryl group having 6 to 20 carbon atoms, a substituted or unsubstituted alkyloxycarbonyl group having 2 to 10 carbon atoms, a substituted or unsubstituted aryloxycarbonyl group having 7 to 10 carbon atoms, a substituted or unsubstituted alkylaminocarbonyl group having 2 to 10 carbon atoms, a substituted or unsubstituted arylaminocarbonyl group having 7 to 10 carbon atoms, a substituted or unsubstituted alkylsulfonyl group having 1 to 10 carbon atoms, a substituted or unsubstituted arylsulfonyl group having 6 to 10 carbon atoms, or a cyano group, more preferably a substituted or unsubstituted aryl group having 6 to 20 carbon atoms, a substituted or unsubstituted alkyloxycarbonyl group having 2 to 10 carbon atoms, a substituted or unsubstituted aryloxycarbonyl group having 7 to 10 carbon atoms, a substituted or unsubstituted alkylsulfonyl group having 1 to 10 carbon atoms, a substituted or unsubstituted arylsulfonyl group having 6 to 10 carbon atoms, or a cyano group, further preferably a substituted or unsubstituted alkyloxycarbonyl group having 2 to 10 carbon atoms, a substituted or unsubstituted aryloxycarbonyl group having 7 to 10 carbon atoms, a substituted or unsubstituted alkylsulfonyl group having 1 to 10 carbon atoms, a substituted or unsubstituted arylsulfonyl group having 6 to 10 carbon atoms, or a cyano group, and is particularly preferably a cyano group.

$R^2$ is preferably a hydrogen atom, a substituted or unsubstituted alkyl group having 1 to 10 carbon atoms, or a substituted or unsubstituted aryl group having 6 to 10 carbon atoms, and is more preferably a substituted or unsubstituted alkyl group having 1 to 10 carbon atoms or a substituted or unsubstituted aryl group having 6 to 10 carbon atoms in view of solubility. The alkyl group is preferably a branched alkyl group having 3 to 6 carbon atoms, more preferably a tertiary alkyl group having 4 to 6 carbon atoms.

$L^{2-}$ represents the divalent azo dye anion provided by eliminating the dissociative hydrogen atom in Q and the hydrogen atom in the —NH— group marked with asterisk * from the azo dye represented by the general formula (1-1) or (1-2).

It is preferred that the azo-metal complex dye represented by the general formula (A) is further represented by the general formula (2-1) or (3-1).

The general formula (2-1) is described below. M represents a metal ion, and the meaning and preferred embodiments thereof are the same as described above.

$L^1$ is equal to $L'$.

$Q^2$ represents an atomic group forming a nitrogen-containing heterocycle. The nitrogen-containing heterocyclic group formed by $Q^2$ is preferably represented by any one of the following structural formulae (q-1) to (q-4), more preferably represented by the formula (q-1) or (q-2), and further preferably represented by the formula (q-1).

The details such as specific examples and preferred embodiments of $R^{101}$ and $R^{102}$ are the same as those of $R^1$. The details such as specific examples and preferred embodiments of $R^{103}$ and $R^{104}$ are the same as those of $R^2$.

The meanings and preferred embodiments of $R^6$ and $R^7$ in the general formula (2-1) are the same as those of $R^6$ and $R^7$ in the general formula (1-1).

q is an integer of 1 to 4, preferably 1 or 2.
n1 is 1 or 2, preferably 2.
n2 is an integer of 0 to 3, preferably an integer of 0 to 2, more preferably 0 or 1.
n3 represents a value of q/p within a range of 0<n3≦4.
p is an integer of 1 to 10, preferably an integer of 1 to 4, more preferably an integer of 1 to 3, further preferably 1 or 2.

Specific examples of the azo-metal complex dyes represented by the general formula (2-1) are illustrated below without intention of restricting the scope of the present invention.

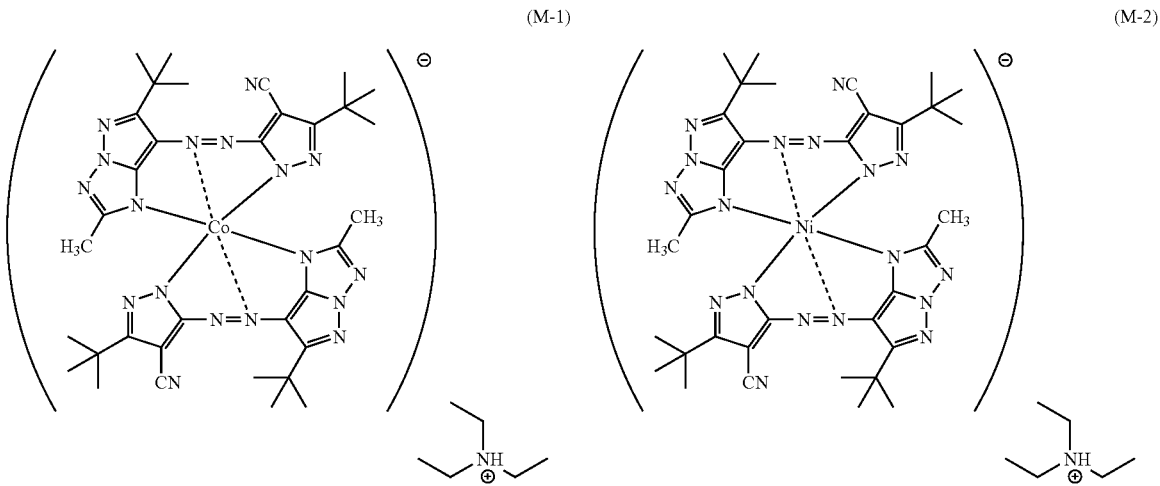

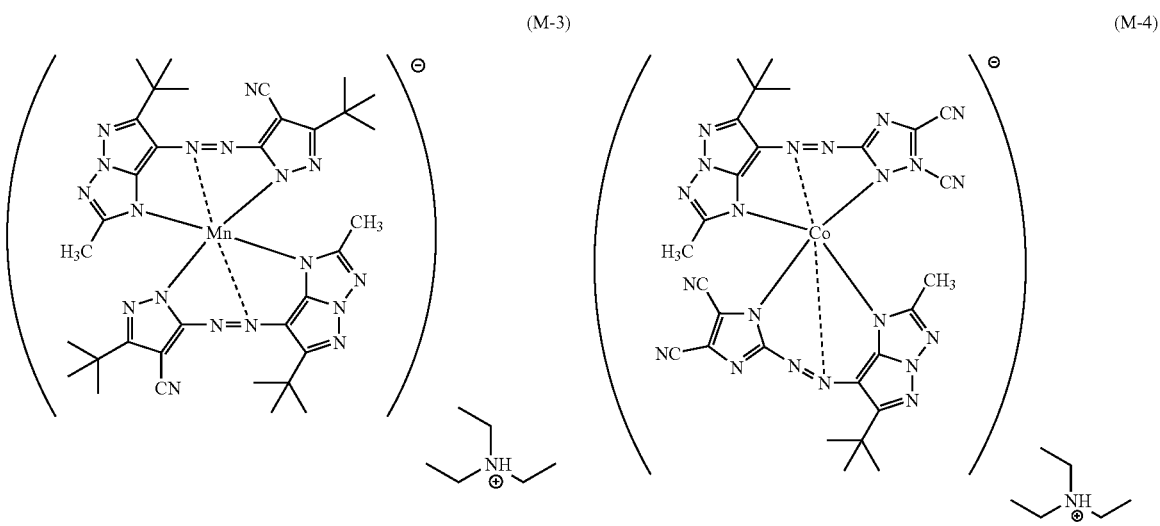

(M-5)
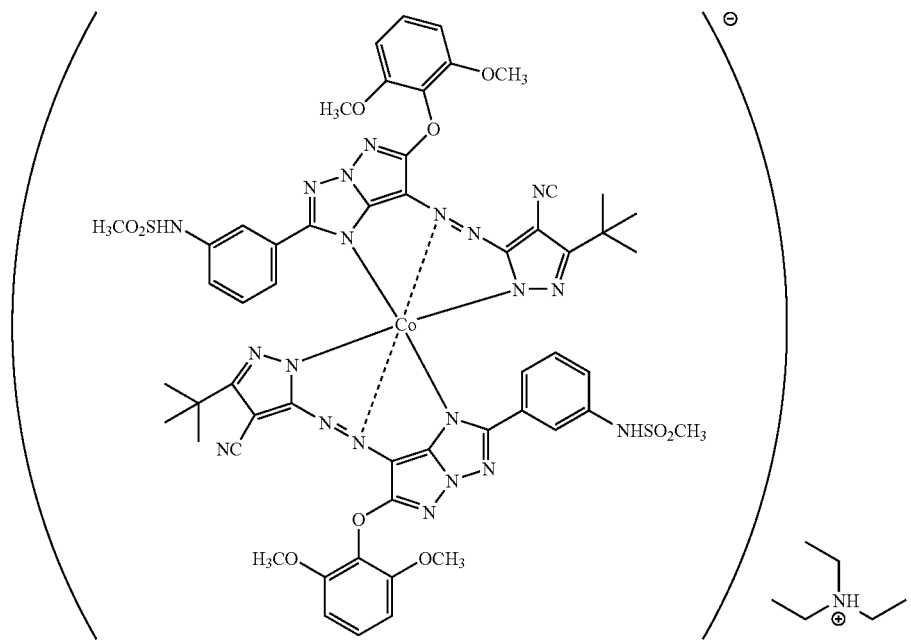
(M-6)
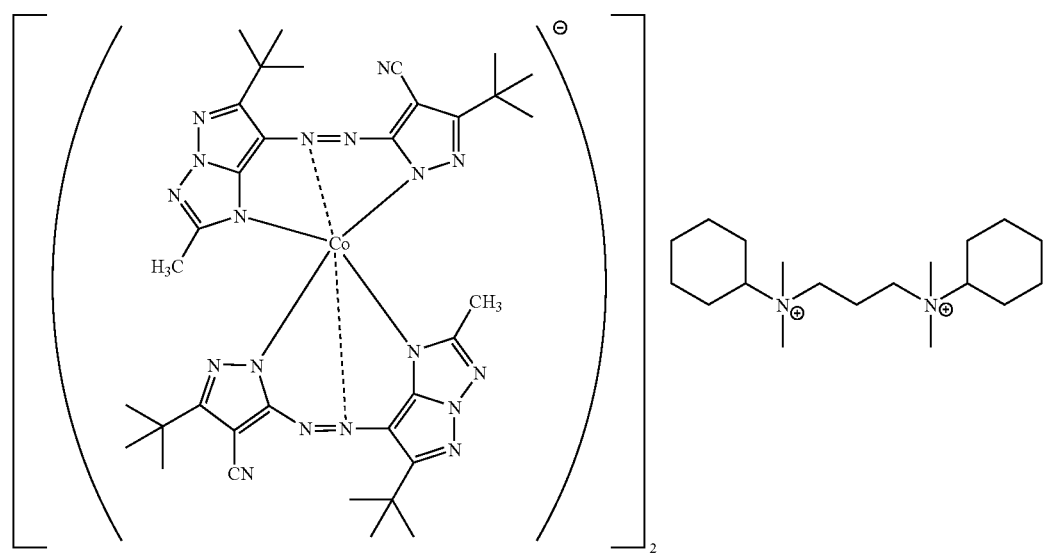

-continued
(M-7)
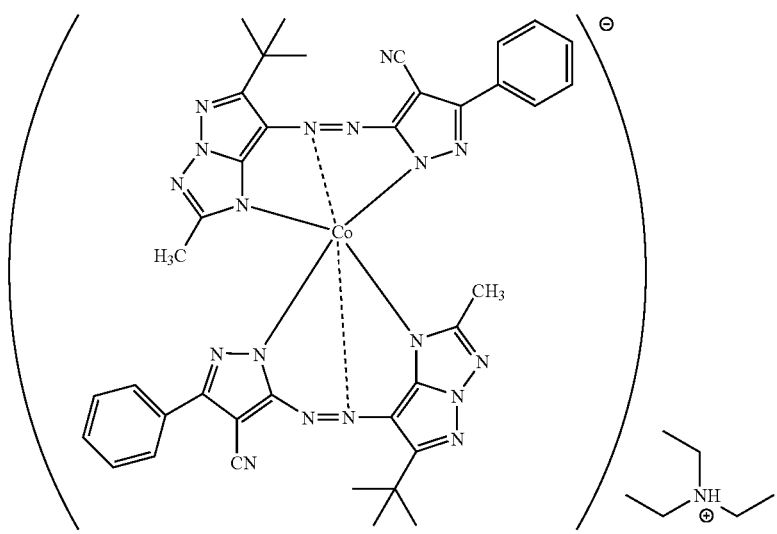
(M-8)
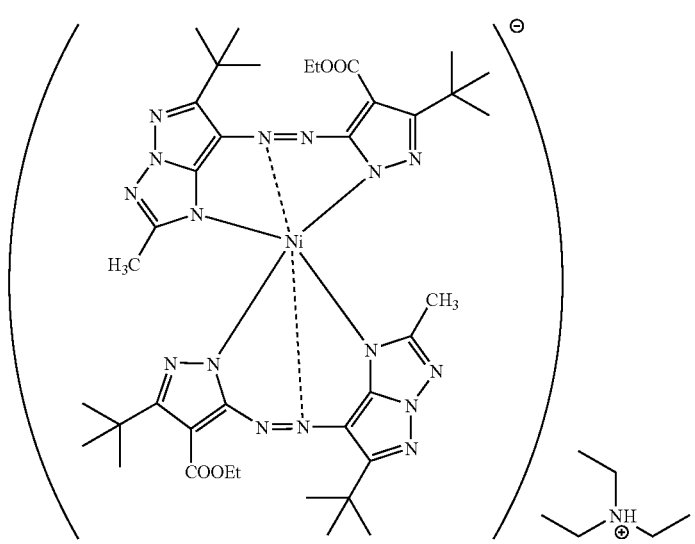
(M-9)
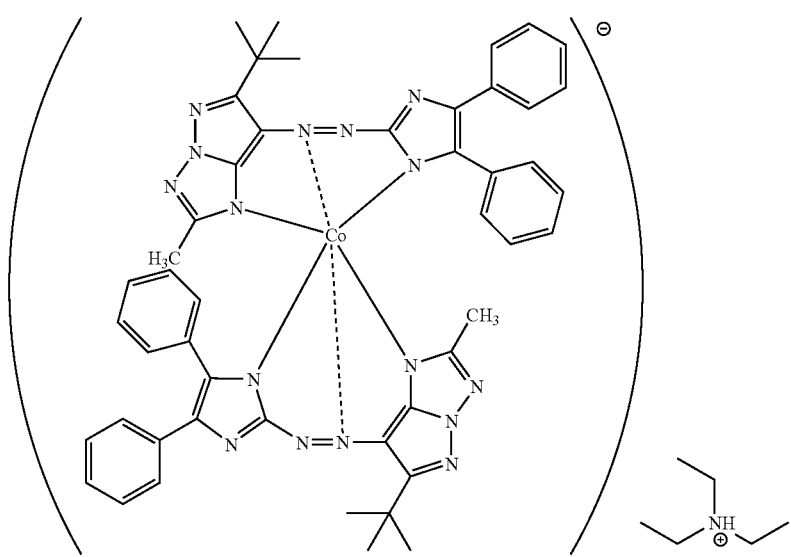

Though the negative charges of the azo ligand are located on the N atoms bonding to M in the general formula (2-1), the positions of the negative charges are not limited thereto. The negative charges may be delocalized over the entire azo ligand skeleton, and may be located to form a tautomeric structure. Also in the azo ligand of the general formula (3-1) hereinafter described, the positions of the negative charges are not limited in the same manner.

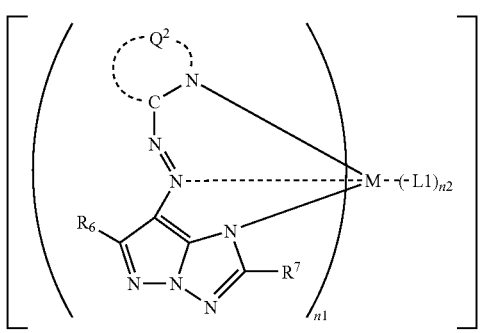

The general formula (3-1) is described below. The meanings and preferred embodiments of M, $Q^2$, $R^6$, L1, n1 to n3, $X^{p+}$, p, and q in the general formula (3-1) are the same as those in the general formula (2-1). The meaning and preferred embodiments of $R^8$ in the general formula (3-1) are the same as those in the general formula (I-2).

Specific examples of the azo-metal complex dyes represented by the general formula (3-1) are illustrated below without intention of restricting the scope of the present invention.

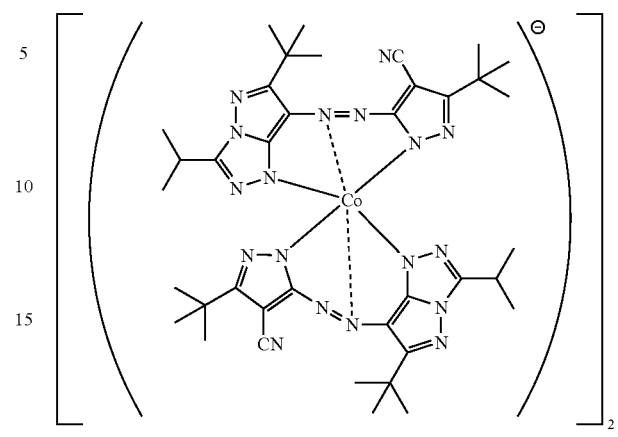

(M-27)

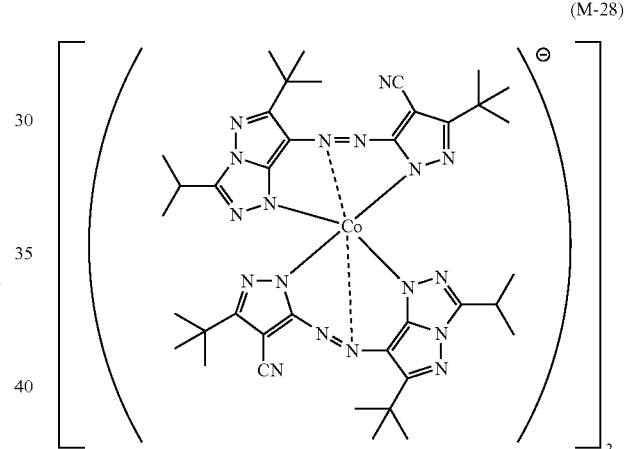

(M-28)

(M-26)

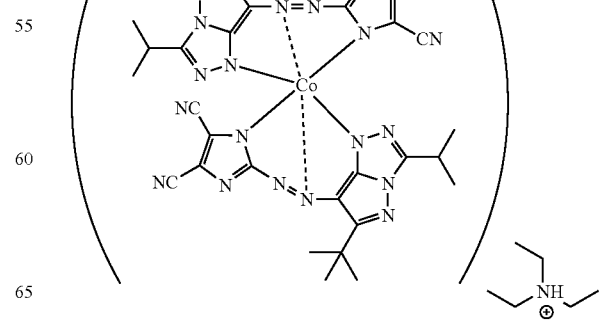

(M-29)

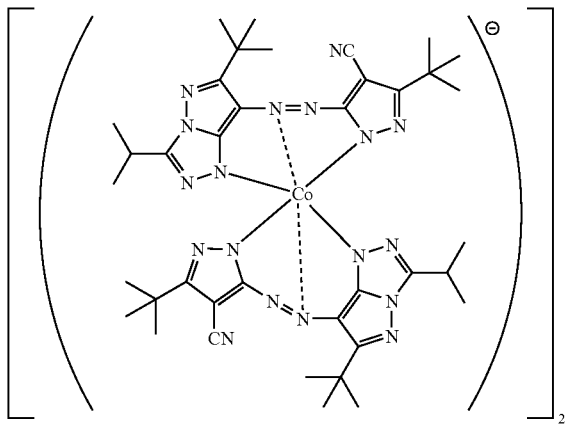

(M-30)

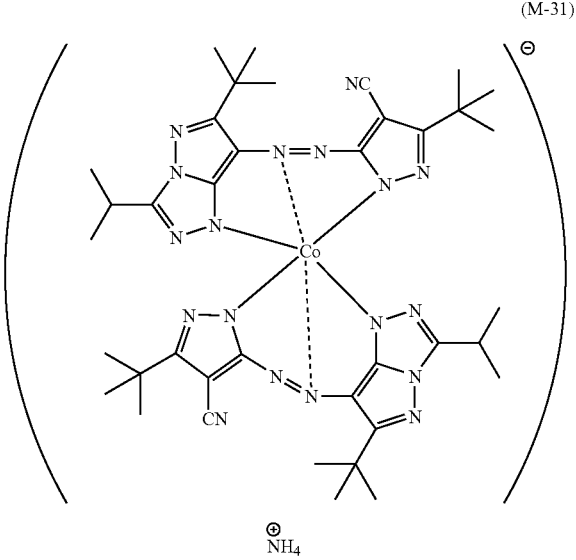

(M-31)

When the metal ion is divalent, the azo-metal complex dye of the present invention is likely to have a coordination structure represented by the general formula (B).

The general formula (B) is described below. The meaning and preferred embodiments of L2− in the general formula (B) are the same as those in the general formula (A). It should be noted that particularly Q in the $L^{2-}$ is preferably a pyrazole ring.

L2 is a neutral ligand, and examples thereof are the same as those of L' in the general formula (A).

M is a divalent metal ion (or a divalent metal oxide ion), preferably $Cu^{2+}$ or $Zn^{2+}$, more preferably $Cu^{2+}$.

s is an integer of 1 to 4, preferably 4.

t is an integer of 0 to 14, preferably an integer of 0 to 6, more preferably an integer of 0 to 4.

u is an integer of 2 to 5, and is equal to or greater than s. u is preferably 5.

$Y^{v-}$ represents a v-valent anion, which is preferably an inorganic or organic anion.

v is an integer of 1 to 10, preferably an integer of 1 to 5, more preferably an integer of 1 to 4, further preferably an integer of 1 to 3, particularly preferably 1 or 2.

The inorganic anion is not particularly limited, and may be a halogen ion, $ClO_4^-$, $PF_6^-$, $OH^-$, $NO_3^-$, $BF_4^-$, $SO_4^{2-}$, etc.

The organic anion is not particularly limited, and may be a substituted or unsubstituted carboxylate anion, a substituted or unsubstituted sulfonate anion, a substituted or unsubstituted sulfinate anion, a substituted or unsubstituted phosphate anion, a substituted or unsubstituted alkoxy anion, a substituted or unsubstituted thioalkoxy anion, a substituted or unsubstituted phenoxy anion, a substituted or unsubstituted thiophenoxy anion, an anion provided by eliminating a proton from a substituted or unsubstituted nitrogen-containing heterocycle (such as pyrrole, pyrazole, or imidazole), a substituted or unsubstituted alkylamino anion, a substituted or unsubstituted anilino anion, a substituted or unsubstituted carbonylamino anion, a substituted or unsubstituted sulfonylamino anion, a thiocyanate anion, a substituted or unsubstituted acetylacetonate anion, etc. The organic anion is preferably a substituted or unsubstituted carboxylate anion or a substituted or unsubstituted sulfonate anion, more preferably a substituted or unsubstituted carboxylate anion.

w represents a value within a range of $0<w\leq 4$ obtained by dividing the positive charge number in the general formula (B) by v.

The general formula (C) is described below. $L^{2-}$ in the general formula (C) is the divalent azo dye anion derived from the compound represented by the general formula (1-1) or (1-2), wherein Q being a substituted or unsubstituted pyrazole ring group. $L^{2-}$ in the general formula (C) is preferably from the compound represented by the general formula (1-1).

In the general formula (C), each of $R^6$ to $R^8$ is an alkyl or aryl group, preferably a substituted or unsubstituted alkyl group having 1 to 10 carbon atoms or a substituted or unsubstituted aryl group having 6 to 20 carbon atoms, more preferably a substituted or unsubstituted alkyl group having 1 to 6 carbon atoms, further preferably a substituted or unsubstituted alkyl group having 1 to 4 carbon atoms.

The pyrazole ring of Q preferably has two substituents on the ring, and examples of the substituents are the same as those of $R^6$ to $R^8$. One of the substituents on the pyrazole ring is preferably a group selected from a cyano group, alkoxycarbonyl groups, and alkylsulfonyl groups, more preferably a group selected from a cyano group and alkylsulfonyl groups, further preferably a cyano group. The other substituent on the pyrazole ring is preferably a substituted or unsubstituted alkyl group having 1 to 10 carbon atoms or a substituted or unsubstituted aryl group having 6 to 20 carbon atoms, more preferably a substituted or unsubstituted alkyl group having 1 to 6 carbon atoms, further preferably a substituted or unsubstituted alkyl group having 1 to 4 carbon atoms.

In the general formula (C), it is preferred that each of $R^6$ to $R^8$ is a substituted or unsubstituted alkyl group having 1 to 10 carbon atoms or a substituted or unsubstituted aryl group having 6 to 20 carbon atoms, one substituent on the pyrazole ring is a cyano group, an alkoxycarbonyl group, or an alkylsulfonyl group, and the other substituent on the pyrazole ring is a substituted or unsubstituted alkyl group having 1 to 10 carbon atoms or a substituted or unsubstituted aryl group having 6 to 20 carbon atoms. It is more preferred that each of $R^6$ to $R^8$ is a substituted or unsubstituted alkyl group having 1 to 6 carbon atoms, one substituent on the pyrazole ring is a cyano group or an alkylsulfonyl group, and the other substituent on the pyrazole ring is a substituted or unsubstituted alkyl group having 1 to 6 carbon atoms. It is further preferred that each of $R^6$ to $R^6$ is a substituted or unsubstituted alkyl group having 1 to 4 carbon atoms, one substituent on the pyrazole ring is a cyano group, and the other substituent on the pyrazole ring is a substituted or unsubstituted alkyl group having 1 to 4 carbon atoms.

In the general formula (C), $(Y^{v-})_w$ is $(Cl^-)_2$, $(Br^-)_2$, $(I^-)_2$, $(ClO_4^-)_2$, $(PF_6^-)_2$, $(BF_4^-)_2$, $SO_4^{2-}$, or $(CH_3COO^-)_2$, preferably $(Cl^-)_2$, $(ClO_4^-)_2$, $SO_4^{2-}$, or $(CH_3COO^-)_2$, more preferably $(Cl^-)_2$, $(ClO_4^-)_2$, or $(CH_3COO^-)_2$, further preferably $(Cl^-)_2$ or $(CH_3COO^-)_2$.

Specific examples of the azo-metal complex dyes represented by the general formula (B) are illustrated below without intention of restricting the scope of the present invention.

TABLE 1

Azo-metal complex dye represented by general formula (B)

(s = 4, t = 0, u = 5)

| Compound Examples | M | $L^{2-}$ | $(Y^{v-})_w$ |
|---|---|---|---|
| (M-13) | $Cu^{2+}$ | [structure] | $(CH_3COO^-)_2$ |
| (M-14) | $Cu^{2+}$ | [structure with H$_3$CO$_2$SHN-phenyl substituent] | $(ClO_4^-)_2$ |
| (M-15) | $Cu^{2+}$ | [structure] | $SO_4^{2-}$ |
| (M-16) | $Cu^{2+}$ | [structure] | $(Cl^-)_2$ |

TABLE 1-continued

Azo-metal complex dye represented by general formula (B)
(s = 4, t = 0, u = 5)

| Compound Examples | M | $L^{2-}$ | $(Y^{v-})_w$ |
|---|---|---|---|
| (M-17) | $Cu^{2+}$ | | $(PF_4^-)_2$ |
| (M-18) | $Cu^{2+}$ | | (naphthalene-2,6-diol-3,7-disulfonate) |
| (M-19) | $Cu^{2+}$ | | $(CH_3COO^-)_2$ |

TABLE 2

Azo-metal complex dye represented by general formula (B)
(s = 4, t = 0, u = 5)

| Compound Examples | M | $L^{2-}$ | $(Y^{v-})_w$ |
|---|---|---|---|
| (M-20) | $Cu^{2+}$ | | $(CH_3COO^-)_2$ |

TABLE 2-continued

Azo-metal complex dye represented by general formula (B)
(s = 4, t = 0, u = 5)

| Compound Examples | M | L²⁻ | (Yᵛ⁻)_w |
|---|---|---|---|
| (M-21) | $Cu^{2+}$ | [structure: pyrazolo-triazole with phenyl and methyl substituents, azo-linked to pyrazole bearing CN and phenyl groups] | $(CH_3COO^-)_2$ |
| (M-22) | $Cu^{2+}$ | [structure: pyrazolo-triazole with tert-butyl and methyl substituents, azo-linked to pyrazole bearing CN and phenyl groups] | $SO_4^{2-}$ |
| (M-23) | $Cu^{2+}$ | [structure: pyrazolo-triazole with phenyl and methyl substituents, azo-linked to pyrazole bearing CN and tert-butyl groups] | $(ClO_4^-)_2$ |
| (M-24) | $Cu^{2+}$ | [structure: pyrazolo-triazole substituted with 2,6-dimethoxyphenoxy group and 3-(methanesulfonamido)phenyl group, azo-linked to pyrazole bearing CN and tert-butyl groups] | $(CH_3COO^-)_2$ |

TABLE 2-continued

Azo-metal complex dye represented by general formula (B)
(s = 4, t = 0, u = 5)

| Compound Examples | M | L²⁻ | (Yᵛ⁻)_w |
|---|---|---|---|
| (M-25) | Cu²⁺ | (structure) | (CH₃COO⁻)₂ |
| (M-32) | Cu²⁺ | (structure) | (CH₃COO⁻)₂ |

TABLE 3

Azo-metal complex dye represented by general formula (B)
(s = 4, t = 0, u = 5)

| Compound Examples | M | L²⁻ | (Yᵛ⁻)_w |
|---|---|---|---|
| (M-33) | Cu²⁺ | (structure) | (CH₃COO⁻)₂ |
| (M-34) | Cu²⁺ | (structure) | (CH₃COO⁻)₂ |

TABLE 3-continued

Azo-metal complex dye represented by general formula (B)
(s = 4, t = 0, u = 5)

| Compound Examples | M | L$^{2-}$ | (Y$^{v-}$)$_w$ |
|---|---|---|---|
| (M-35) | Cu$^{2+}$ | | SO$_4^{2-}$ |
| (M-36) | Cu$^{2+}$ | | (ClO$_4^-$)$_2$ |
| (M-37) | Cu$^{2+}$ | | (CH$_3$COO$^-$)$_2$ |
| (M-38) | Cu$^{2+}$ | | (BF$_4^-$)$_2$ |
| (M-39) | Cu$^{2+}$ | | (CH$_3$COO$^-$)$_2$ |
| (M-40) | Cu$^{2+}$ | | (I$^-$)$_2$ |

Though the azo-metal complex dyes of the general formula (B), including the compounds (M-13) to (M-40), are illustrated such that the negative charges of the azo ligand are located on the N atoms bonding to M, the positions of the negative charges are not limited thereto. The negative charges may be delocalized over the entire azo ligand skeleton, and may be located to form a tautomeric structure.

Furthermore, in the compounds of the general formula (B) including the compounds (M-13) to (M-40), t may vary depending on the surrounding conditions. Thus, when the compound is in the presence of the ligand of L' or the like, the ligand may be incorporated into the compound.

The compound of the general formula (B) may be changed depending on the surrounding conditions, and thus the valence of the copper ion may be changed. For example, $Cu^{2+}$ may be converted to $Cu^+$ in the presence of a solvent, and in this case the azo-metal complex moiety may be neutral or anionic. Further, the number of $Y^{v-}$ may be changed, and $Y^{v-}$ may be replaced by a cation such as $X^{p+}$ in the general formula (A).

Then, the structure of the optical information recording medium according to the present invention is described below.

Embodiments (1) and (2) are described as preferred embodiments of the optical information recording medium according to the present invention.

Embodiment (1): An optical information recording medium containing a dye-containing WORM-type recording layer and a cover layer having a thickness of 0.01 to 0.5 mm disposed in this order on a substrate having a thickness of 0.7 to 2 mm.

Embodiment (2): An optical information recording medium containing a dye-containing WORM-type recording layer and a protective substrate having a thickness of 0.1 to 1.0 mm disposed in this order on a substrate having a thickness of 0.1 to 1.0 mm.

In Embodiment (1), it is preferred that the substrate has pregrooves with a track pitch of 50 to 500 nm, a groove width of 25 to 250 nm, and a groove depth of 5 to 150 nm. In Embodiment (2), it is preferred that the substrate has pregrooves with a track pitch of 200 to 500 nm, a groove width of 50 to 300 nm, a groove depth of 30 to 150 nm, and a wobble amplitude of 5 to 50 nm.

[Optical Information Recording Medium of Embodiment (1)]

The optical information recording medium of Embodiment (1) has at least the substrate, the WORM-type recording layer, and the cover layer. A specific example of the optical information recording medium of Embodiment (1) is shown in FIG. 1. As shown in FIG. 1, an optical information recording medium 10A has a substrate 12, and has a light reflection layer 18, a WORM-type recording layer 14, a barrier layer 20, an adhesion layer or tacky layer 22, and a cover layer 16 disposed in this order on the substrate 12. The components are described below.

[Substrate 12]

In Embodiment (1), the substrate 12 has pregrooves 34 (guide grooves) having particular track pitch, groove width (half width), groove depth, and wobble amplitude within the following ranges. The pregrooves 34 are formed to achieve a recording density higher than those of CD-R and DVD-R, and are suitable, for example, for optical information recording media using bluish purple laser lights.

The track pitch of the pregrooves 34 is 50 to 500 nm. The track pitch is preferably 420 nm or less, more preferably 370 nm or less, further preferably 330 nm or less. Further, the track pitch is preferably 100 nm or more, more preferably 200 nm or more, further preferably 260 nm or more. When the track pitch is 50 nm or more, the pregrooves 34 can be formed accurately to prevent crosstalk. When the track pitch is 500 nm or less, high-density recording can be achieved.

The track pitch of the pregrooves is preferably 100 to 420 nm, more preferably 200 to 370 nm, further preferably 260 to 330 nm.

The groove width (the half width, which is a width at half the groove depth) of the pregroove is 25 to 250 nm. The groove width is preferably 240 nm or less, more preferably 230 nm or less, further preferably 220 nm or less. Further, the groove width is preferably 50 nm or more, more preferably 80 nm or more, further preferably 100 nm or more. When the groove width of the pregroove 34 is 25 nm or more, the groove can be sufficiently transferred in a forming process, and the error rate increase can be prevented in a recording process. When the groove width is 250 nm or less, the groove can be sufficiently transferred in a forming process, and crosstalk due to pit expansion can be prevented in a recording process.

The groove width (the half width) of each pregroove is preferably 50 to 240 nm, more preferably 80 to 230 nm, further preferably 100 to 220 nm.

The groove depth of each pregroove 34 is 5 to 150 nm. The groove depth is preferably 85 nm or less, more preferably 80 nm or less, further preferably 75 nm or less. Further, the groove depth is preferably 10 nm or more, more preferably 20 nm or more, further preferably 28 nm or more. When the groove depth of the pregroove is 5 nm or more, a sufficient recording modulation can be obtained. When the groove depth is 150 nm or less, a high reflectance can be obtained.

The groove depth of each pregroove is preferably 10 to 85 nm, more preferably 20 to 80 nm, further preferably 28 to 75 nm.

The groove inclination angle of the pregroove 34 is preferably 80° or less, more preferably 75° or less, further preferably 70° or less, particularly preferably 65° or less. Further, the groove inclination angle is preferably 20° or more, more preferably 30° or more, further preferably 40° or more.

When the groove inclination angle of the pregroove 34 is 20° or more, a sufficient tracking error signal amplitude can be obtained. When the groove inclination angle is 80° or less, excellent formability can be achieved.

[Worm-Type Recording Layer 14]

In Embodiment (1), the WORM-type recording layer 14 may be formed by the steps of dissolving a dye in a solvent together with or without a binder to prepare a coating liquid, applying the coating liquid to the substrate or the light reflection layer to be hereinafter described, and drying the applied coating layer. The WORM-type recording layer may have a single- or multi-layer structure, and the step of applying a coating liquid is repeatedly carried out to form such a multi-layer structure.

The concentration of the dye in the coating liquid is generally 0.01% to 15% by mass, preferably 0.1% to 10% by mass, more preferably 0.5% to 5% by mass, most preferably 0.5% to 3% by mass.

Examples of the solvents for preparing the coating liquid include esters such as butyl acetate, ethyl lactate, and cellosolve acetate; ketones such as methyl ethyl ketone, cyclohexanone, and methyl isobutyl ketone; chlorinated hydrocarbons such as dichloromethane, 1,2-dichloroethane, and chloroform; amides such as dimethylformamide; hydrocarbons such as methylcyclohexane; ethers such as tetrahydrofuran, ethyl ether, and dioxane; alcohols such as ethanol, n-propanol, isopropanol, n-butanol, and diacetone alcohol; fluorine-containing solvents such as 2,2,3,3-tetrafluoro-1-propanol; and glycol ethers such as ethylene glycol monomethyl ether, ethylene glycol monoethyl ether, and propylene glycol monomethyl ether.

The solvents may be used singly or as a mixture of two or more in view of the solubility of the dye. Various additives such as binders, antioxidants, UV absorbers, plasticizers, and lubricants may be added to the coating liquid in accordance with the purpose.

Examples of methods for applying the coating liquid include spray methods, spin coating methods, dipping methods, roll coating methods, blade coating methods, doctor roll methods, and screen printing methods. Preferred among them are spin coating methods.

In the applying step, the temperature of the coating liquid is preferably 23° C. to 50° C., more preferably 24° C. to 40° C.

On a land 38 (a convex portion of the substrate 12), the thickness of the WORM-type recording layer 14 is preferably 300 nm or less, more preferably 250 nm or less, further preferably 200 nm or less, particularly preferably 180 nm or less. Further, the thickness is preferably 1 nm or more, more preferably 3 nm or more, further preferably 5 nm or more, particularly preferably 7 nm or more.

On a groove 40 (a concave portion of the substrate 12), the thickness of the WORM-type recording layer 14 is preferably 400 nm or less, more preferably 300 nm or less, further preferably 250 nm or less. Further, the thickness is preferably 10 nm or more, more preferably 20 nm or more, further preferably 25 nm or more.

The ratio of the thickness of the WORM-type recording layer 14 on the land 38 to the thickness of the WORM-type recording layer 14 on the groove 40 is preferably 0.1 or more, more preferably 0.13 or more, further preferably 0.15 or more, particularly preferably 0.17 or more. The ratio is preferably less than 1, more preferably 0.9 or less, further preferably 0.85 or less, particularly preferably 0.8 or less.

Various anti-fading agents may be added to the WORM-type recording layer 14 to increase the light fastness of the layer. In general, the anti-fading agent is a singlet oxygen quencher. The light fastness may be further improved by adding the singlet oxygen quencher in the present invention. The singlet oxygen quencher may be selected from those described in known publications such as patent publications.

Specific examples of the singlet oxygen quenchers are described in Japanese Laid-Open Patent Publication Nos. 58-175693, 59-81194, 60-18387, 60-19586, 60-19587, 60-35054, 60-36190, 60-36191, 60-44554, 60-44555, 60-44389, 60-44390, 60-54892, 60-47069, 63-209995, and 4-25492; Japanese Patent Publication Nos. 1-38680 and 6-26028; Germany Patent No. 350399; Nippon Kagakukai-shi, 1992, October issue, Page 1141; etc.

The ratio of the anti-fading agent such as the singlet oxygen quencher to the dye is generally 0.1% to 50% by mass, preferably 0.5% to 45% by mass, further preferably 3% to 40% by mass, particularly preferably 5% to 25% by mass.

[Cover Layer 16]

In Embodiment (1), the cover layer 16 is generally bonded to the WORM-type recording layer 14 or the barrier layer 20 as shown in FIG. 1 by the adhesion layer or tacky layer 22.

The cover layer 16 is not particularly limited as long as it is a transparent film, and preferred examples of the materials for the transparent film include acrylic resins such as polycarbonates and polymethyl methacrylates; vinyl chloride resins such as polyvinyl chlorides and vinyl chloride copolymers; epoxy resins; amorphous polyolefins; polyesters; and cellulose triacetates. More preferred examples are polycarbonates and cellulose triacetates.

The term "transparent" means that the transmittance of a light for recording and reproducing is 80% or more.

Various additives may be added to the cover layer 16 as long as they do not interfere with the advantageous effects of the present invention. For example, the cover layer 16 may contain a UV absorber for blocking out lights with wavelengths of 400 nm or less and/or a dye for blocking out lights with wavelengths of 500 nm or more.

The surface physical properties of the cover layer 16 are preferably such that the surface roughness is 5 nm or less in both the 2- and 3-dimensional roughness parameters.

It is preferred that the birefringence of the cover layer 16 is 10 nm or less from the viewpoint of the property of concentrating a light used for recording and reproducing.

The thickness of the cover layer 16 may be determined depending on the NA and the wavelength of a laser light 46 for recording and reproducing. In the present invention, the thickness is preferably 0.01 to 0.5 mm, more preferably 0.05 to 0.12 mm.

The total thickness of the cover layer 16 and the adhesion layer or tacky layer 22 is preferably 0.09 to 0.11 mm, more preferably 0.095 to 0.105 mm.

A protective layer (such as a hard coat layer 44 shown in FIG. 1) may be formed on the light incident surface of the cover layer 16 to prevent the surface from being scratched in the production of the optical information recording medium 10A.

To stick the cover layer 16 on the WORM-type recording layer 14 or barrier layer 20, the adhesion layer or tacky layer 22 may be formed between the layers.

The adhesion layer contains an adhesive, and preferred examples of the adhesives include UV curing resins, EB curing resins, and thermosetting resins.

In the case of using the UV curing resin as the adhesive, the UV curing resin may be directly applied onto the barrier layer 20. Alternatively, the UV curing resin may be dissolved in an appropriate solvent such as methyl ethyl ketone or ethyl acetate, and thus-obtained coating liquid may be added to a dispenser and applied therefrom to the barrier layer 20. It is preferred that the UV curing resin for the adhesion layer has a small cure shrinkage ratio from the viewpoint of preventing curling of the optical information recording medium. Examples of such UV curing resins include SD-640 available from Dainippon Ink and Chemicals, Inc.

The method for forming the adhesion layer is not particularly limited, and the adhesion layer is preferably formed by the steps of applying a predetermined amount of adhesive to a surface of the barrier layer 20 or the WORM-type recording layer 14, to which surface the cover layer is to be attached, placing the cover layer 16 thereon, spreading the adhesive between the surface and the cover layer 16 uniformly by spin coating, and hardening the adhesive.

The thickness of the adhesion layer is preferably 0.1 to 100 µm, more preferably 0.5 to 50 µm, further preferably 1 to 30 µm.

The tacky layer contains a tackiness agent, and examples thereof include acrylate-, rubber-, or silicon-based tackiness agents. The acrylate-based tackiness agents are preferred from the viewpoints of transparency and durability. The acrylate-based tackiness agent is preferably a copolymer of a main component such as 2-ethylhexyl acrylate or n-butyl acrylate with a short-chain component and a crosslinking point component for increasing cohesion force. The short-chain component may be an alkyl acrylate or methacrylate such as methyl acrylate, ethyl acrylate, or methyl methacrylate, and the crosslinking point component may be acrylic acid, methacrylic acid, an acrylamide derivative, maleic acid, hydroxylethyl acrylate, glycidyl acrylate, or the like. By appropriately selecting the mixing ratio and types of the main component, the short-chain component, and the crosslinking point component, the glass-transition temperature (Tg) and the crosslinking density of the tackiness agent can be controlled.

The method for forming the tacky layer is not particularly limited, and the tacky layer may be formed by the steps of applying a predetermined amount of tackiness agent uniformly to a surface of the barrier layer 20 or the WORM-type recording layer 14, to which surface the cover layer is to be attached, placing the cover layer 16 thereon, and hardening the tackiness agent. Alternatively, the tacky layer may be formed by the steps of applying a predetermined amount of tackiness agent uniformly to one surface of the cover layer 16 to form a tackiness agent coating, sticking the coating on the surface, to which the cover layer is to be attached, and hardening the coating.

A commercially-available tacky film containing a cover layer 16 and a tacky layer may be used.

The thickness of the tacky layer is preferably 0.1 to 100 more preferably 0.5 to 50 µm, further preferably 10 to 30 µm.

The cover layer may be formed by a spin coating method using a UV curing resin.

[Other Layers]

The optical information recording medium 10A of Embodiment (1) may have another layer in addition to the essential layers as long as it does not interfere with the advantageous effects of the present invention. Examples of such layers include a label layer having a desired image, which is formed on the back surface of the substrate 12 (the side opposite to the surface on which the WORM-type recording layer 14 is formed); a light reflection layer 18 (to be hereinafter described in detail) which is formed between the substrate 12 and the WORM-type recording layer 14; a barrier layer 20 (to be hereinafter described in detail) which is formed between the WORM-type recording layer 14 and the cover layer 16; and an interface layer, formed between the light reflection layer 18 and the WORM-type recording layer 14. The label layer may be composed of an ultraviolet curing resin, a thermosetting resin, a heat-drying resin, or the like.

The above essential layers and additional layers may have a single- or multi-layer structure.

In the optical information recording medium 10A of Embodiment (1), it is preferred that the light reflection layer 18 is formed between the substrate 12 and the WORM-type recording layer 14 to increase the reflectance to the laser light 46 and to improve the recording/reproducing properties.

For example, the light reflection layer 18 may be formed on the substrate by vacuum-depositing, sputtering, or ion-plating a light reflective substance having a high reflectance to the laser light 46.

The thickness of the light reflection layer 18 is generally 10 to 300 nm, preferably 30 to 200 nm.

The reflectance is preferably 70% or more.

Examples of the light reflective substances with high reflectance include metals and metalloids of Mg, Se, Y, Ti, Zr, Hf, V, Nb, Ta, Cr, Mo, W, Mn, Re, Fe, Co, Ni, Ru, Rh, Pd, Ir, Pt, Cu, Ag, Au, Zn, Cd, Al, Ga, In, Si, Ge, Te, Pb, Po, Sn, Bi, etc., and stainless steels. These light reflective substances may be used singly or in combination, or as an alloy. The light reflective substance is preferably Cr, Ni, Pt, Cu, Ag, Au, Al, or a stainless steel, particularly preferably Au, Ag, Al, or an alloy thereof, most preferably Au, Ag, or an alloy thereof.

[Barrier Layer 20 (Intermediate Layer)]

As shown in FIG. 1, in the optical information recording medium 10A of Embodiment (1), the barrier layer 20 is preferably formed between the WORM-type recording layer 14 and the cover layer 16.

The barrier layer 20 can act to increase the storability of the WORM-type recording layer 14, increase the adhesion between the WORM-type recording layer 14 and the cover layer 16, control the reflectance, and control the heat conductivity.

The material of the barrier layer 20 is not particularly limited as long as it can transmit the light for recording and reproducing and can provide the above functions. For example, in general, the material is preferably a dielectric substance having a low gas and water permeability.

Specifically, the material preferably contains a nitride, oxide, carbide, or sulfide of Zn, Si, Ti, Te, Sn, Mo, Ge, Nb, Ta, or the like, more preferably contains $MoO_2$, $GeO_2$, TeO, $SiO_2$, $TiO_2$, ZnO, $SnO_2$, ZnO—$Ga_2O_3$, $Nb_2O_5$, or $Ta_2O_5$, further preferably contains $SnO_2$, ZnO—$Ga_2O_3$, $SiO_2$, $Nb_2O_5$, or $Ta_2O_5$.

The barrier layer 20 may be formed by a vacuum film forming method such as vacuum deposition, DC sputtering, RF sputtering, or ion plating. The barrier layer 20 is preferably formed by a sputtering method.

The thickness of the barrier layer 20 is preferably 1 to 200 nm, more preferably 2 to 100 nm, further preferably 3 to 50 nm.

[Optical Information Recording Medium of Embodiment (2)]

The optical information recording medium of Embodiment (2) has at least the substrate, the WORM-type recording layer, and the protective substrate, and is preferably a laminate type optical information recording medium. Typical layer structures of the optical information recording medium are as follows:

(1) a first layer structure, where a WORM-type recording layer, a light reflection layer, and an adhesion layer are formed in this order on a substrate, and a protective substrate is disposed on the adhesion layer;

(2) a second layer structure, where a WORM-type recording layer, a light reflection layer, a protective layer, and an adhesion layer are formed in this order on a substrate, and a protective substrate is disposed on the adhesion layer;

(3) a third layer structure, where a WORM-type recording layer, a light reflection layer, a protective layer, an adhesion layer, and a protective layer are formed in this order on a substrate, and a protective substrate is disposed on the protective layer;

(4) a fourth layer structure, where a WORM-type recording layer, a light reflection layer, a protective layer, an adhesion layer, a protective layer, and a light reflection layer are formed in this order on a substrate, and a protective substrate is disposed on the light reflection layer; and (5) a fifth layer structure, where a WORM-type recording layer, a light reflection layer, an adhesion layer, and a light reflection layer are formed in this order on a substrate, and a protective substrate is disposed on the light reflection layer.

The above first to fifth layer structures of (1) to (5) are considered to be illustrative, and the layer structure of the optical information recording medium is not limited thereto. A part of the first to fifth layer structures may be replaced or removed. The WORM-type recording layer may be formed also on the protective substrate, and in this case, the resultant optical information recording medium is capable of recording and reproducing on both surfaces. The above-described layers may have a single- or multi-layer structure.

Figure 2:
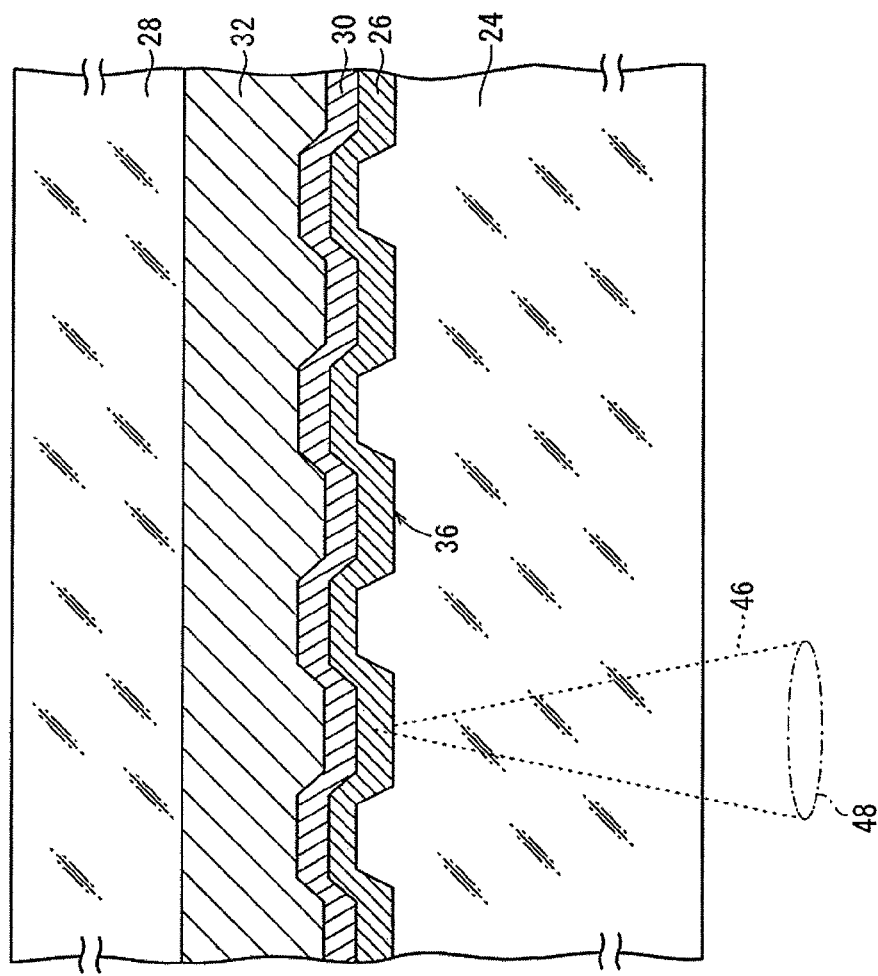
FIG. 2 is a schematic cross-sectional view showing an example of an optical information recording medium according to Embodiment (2).

An example of the optical information recording medium of Embodiment (2), which contains a substrate, a WORM-type recording layer, a light reflection layer, an adhesion layer, and a protective substrate in this order, is described in detail below. A specific optical information recording medium having such a structure is shown in FIG. 2. The optical information recording medium 10B shown in FIG. 2 has a substrate 24, and a WORM-type recording layer 26, a light reflection layer 30, an adhesion layer 32, and a protective substrate 28 are disposed in this order on the substrate 24.

[Substrate 24]

In Embodiment (2), the substrate 24 has pregrooves 36 (guide grooves) having particular track pitch, groove width (half width), groove depth, and wobble amplitude within the following ranges. The pregrooves 36 are formed to achieve a recording density higher than those of CD-R and DVD-R, and are suitable, for example, for optical information recording media using bluish purple laser lights.

The track pitch of the pregrooves 36 is 200 to 500 nm. The track pitch is preferably 450 nm or less, more preferably 430 nm or less. Further, the track pitch is preferably 300 nm or more, more preferably 330 nm or more, further preferably 370 nm or more. When the track pitch is 200 nm or more, the pregrooves can be formed accurately to prevent crosstalk. When the track pitch is 500 nm or less, high-density recording can be achieved.

The groove width (the half width) of each pregroove 36 is 50 to 300 nm. The groove width is preferably 290 nm or less, more preferably 280 nm or less, further preferably 250 nm or less. Further, the groove width is preferably 100 nm or more, more preferably 120 nm or more, further preferably 140 nm or more. When the groove width of the pregroove 36 is 50 nm or more, the groove can be sufficiently transferred in a forming process, and the error rate increase can be prevented in a recording process. When the groove width is 300 nm or less, crosstalk due to pit expansion can be prevented in a recording process, and a sufficient modulation can be achieved.

The groove depth of each pregroove 36 is 30 to 150 nm. The groove depth is preferably 140 nm or less, more preferably 130 nm or less, further preferably 120 nm or less. Further, the groove depth is preferably 40 nm or more, more preferably 50 nm or more, further preferably 60 nm or more. When the groove depth of the pregroove 36 is 30 nm or more, a sufficient recording modulation can be obtained. When the groove depth is 150 nm or less, a high reflectance can be obtained.

The thickness of the substrate 24 is generally 0.1 to 1.0 mm, preferably 0.2 to 0.8 mm, more preferably 0.3 to 0.7 mm.

An undercoat layer may be formed on a surface of the substrate 24, on which the WORM-type recording layer 26 is formed, to improve flatness and adhesion.

Examples of materials of the undercoat layer include polymers such as polymethyl methacrylates, acrylic acid-methacrylic acid copolymers, styrene-maleic anhydride copolymers, polyvinyl alcohols, N-methylolacrylamides, styrene-vinyltoluene copolymers, chlorosulfonated polyethylenes, nitrocelluloses, polyvinyl chlorides, chlorinated polyolefins, polyesters, polyimides, vinyl acetate-vinyl chloride copolymers, ethylene-vinyl acetate copolymers, polyethylenes, polypropylenes, and polycarbonates, and surface modifying agents such as silane coupling agents.

The undercoat layer may be formed by dissolving or dispersing the material in an appropriate solvent, and by applying the obtained coating liquid to a surface of the substrate by a coating method such as spin coating, dip coating, or extrusion coating.

The thickness of the undercoat layer is generally 0.005 to 20 µm, preferably 0.01 to 10 µm.

[WORM-Type Recording Layer 26]

The details of the WORM-type recording layer 26 used in Embodiment (2) are the same as those of the WORM-type recording layer 14 used in Embodiment (1).

[Light Reflection Layer 30]

In Embodiment (2), the light reflection layer 30 may be formed on the WORM-type recording layer 26 to increase the reflectance to the laser light 46 and to improve the recording/reproducing properties. The details of the light reflection layer 30 used in Embodiment (2) are the same as those of the light reflection layer 18 used in Embodiment (1).

[Adhesion Layer 32]

In Embodiment (2), the adhesion layer 32 may be formed between the light reflection layer 30 and the protective substrate 28 to increase the adhesion between the light reflection layer 30 and the protective substrate 28 to be hereinafter described.

The adhesion layer 32 is preferably composed of a light curing resin. It is particularly preferred that the light curing resin has a small cure shrinkage ratio from the viewpoint of preventing curling of the resultant disk. Examples of such light curing resins include UV curing resins (UV curing adhesives) such as SD-640 and SD-661 available from Dainippon Ink and Chemicals, Inc.

The adhesion layer 32 preferably has a thickness of 1 to 1000 µm to obtain elasticity.

[Protective Substrate 28]

The material and shape of the protective substrate 28 (a dummy substrate) used in Embodiment (2) may be the same as those of the above described substrate 12. The thickness of the protective substrate 28 is generally 0.1 to 1.0 mm, preferably 0.2 to 0.8 mm, more preferably 0.3 to 0.7 mm.

[Protective Layer]

In the optical information recording medium 10B of Embodiment (2), a protective layer may be formed to physically and chemically protect the light reflection layer 30, the WORM-type recording layer 26, etc. depending on the layer structure.

Examples of materials of the protective layer include inorganic substances such as ZnS, ZnS—$SiO_2$, SiO, $SiO_2$, $MgF_2$, $SnO_2$, and $Si_3N_4$, and organic substances such as thermoplastic resins, thermosetting resins, and UV curing resins.

For example, a plastic material may be extruded into a film and stuck on the light reflection layer by an adhesive to form the protective layer. Alternatively, the protective layer may be formed by vacuum deposition, sputtering, coating, or the like.

In the case of using a thermoplastic or thermosetting resin for the protective layer, the protective layer may be formed by dissolving the resin in an appropriate solvent and by applying and drying the obtained coating liquid. In the case of using a UV curing resin for the protective layer, the protective layer may be formed by applying the UV curing resin or a coating liquid containing the UV curing resin and an appropriate solvent, and by irradiating the applied resin with a UV light to harden the UV curing resin. Various additives such as antistatic agents, antioxidants, and UV absorbers may be added to the coating liquids in accordance with the purpose.

The protective layer generally has a thickness of 0.1 µm to 1 mm.

[Other Layers]

The optical information recording medium 10B of Embodiment (2) may have another layer in addition to the above layers as long as it does not interfere with the advantageous effects of the present invention. The details of such layers in Embodiment (2) are the same as those in Embodiment (1).

The present invention relates further to a method for recording information on the optical information recording medium having the substrate and the recording layer on the substrate. In the information recording method of the present invention, the optical information recording medium of the present invention is irradiated with a laser light, to record information on the recording layer containing at least one azo-metal complex dye derived from the metal ion and the compound of the general formula (1-1) or (1-2).

For example, information may be recorded on the above optical information recording media according to Embodiments (1) and (2) in the following manner.

First, the substrate side or the protective layer side of the optical information recording medium is irradiated with a recording light such as a semiconductor laser light while rotating the optical information recording medium at a constant linear speed (e.g. 0.5 to 10 m/second) or a constant angular speed. By irradiating the light, the optical properties of the recording medium are changed and the information is recorded in portions irradiated with the laser light. In the embodiment of FIG. 1, the recording laser light 46 such as a semiconductor laser light is applied to the cover layer 16 side through a first objective lens 42 (for example, having a numerical aperture NA of 0.85). When the recording medium is irradiated with the laser light 46, the WORM-type recording layer 14 absorbs the laser light 46, is heated locally, and is physically or chemically changed, for example by generation of a pit, whereby the optical properties of the WORM-type recording layer 14 are changed and the information is recorded thereon. In the embodiment of FIG. 2, in the same manner, the recording laser light 46 such as a semiconductor laser light is applied to the substrate 24 side through a second objective lens 48 (for example, having a numerical aperture NA of 0.65). When the recording medium is irradiated with the laser light 46, the WORM-type recording layer 26 absorbs the laser light 46, is heated locally, and is physically or chemically changed, for example by generation of a pit, whereby the optical properties of the WORM-type recording layer 26 are changed and the information is recorded thereon.

In the present invention, it is preferred that the information is recorded by irradiation with a laser light having a wavelength of 440 nm or less. The recording light may be suitably a semiconductor laser light having an emission wavelength of 440 nm or less. The recording light is preferably a bluish purple semiconductor laser light having an emission wavelength of 390 to 415 nm, or a bluish purple SHG laser light having a center emission wavelength 425 nm obtained by treating a semiconductor infrared laser light having a center emission wavelength of 850 nm with an optical waveguide device. It is particularly preferred from the viewpoint of the recording density that the recording light is a bluish purple semiconductor laser light having an emission wavelength of 390 to 415 nm. The recorded information may be reproduced by irradiating the substrate side or the protective layer side of the optical information recording medium with a semiconductor laser light and by detecting the reflected light while rotating the optical information recording medium at the above constant linear speed.

Then, a method for synthesizing the compound according to the present invention is described below.

Examples of methods for synthesizing the azo dye represented by the general formula (1-1) or (1-2) include those described in Japanese Laid-Open Patent Publication Nos. 61-36362 and 2006-57076. The synthesis is not limited thereto, and the azo dye may be synthesized by using another reaction solvent or acid, and may be synthesized by a coupling reaction under the presence of a base such as sodium acetate, pyridine, or sodium hydroxide. A typical example of the method for synthesizing the azo dye according to the present invention is hereinafter described in detail in Examples, using the compound (A-3).

Examples of methods for synthesizing the azo-metal complex dye by a reaction between the azo dye and the metal ion include methods of stirring the azo dye and a metal salt (which may be a metal complex or a metal oxide salt) under the presence of a base in an organic solvent, water, or a mixture thereof. There are no restrictions on the type of the metal salt, the type of the base, the type of the organic solvent or the mixture thereof, the reaction temperature, etc. A typical example of the method for synthesizing the azo-metal complex dye according to the present invention is described below using the example compound (M-1).

In the synthesis method, the azo-metal complex dye represented by the general formula (2-1) or (3-1) can be obtained by reacting a salt of Co, Ni, Fe, etc. with the azo dye represented by the general formula (1-1) or (1-2) in the presence of the base. In a case where the base is not used in the synthesis system, a neutral azo-metal complex such as a comparative compound (C) or (F) or a cationic azo-metal complex containing the azo dye (ligand) without dissociation of hydrogen atoms is obtained generally.

The present invention is described more specifically below with reference to Examples without intention of restricting the scope of the invention.

Synthesis of the azo dye represented by the general formula (1-1) or (1-2) is described below without intention of restriction.

[Synthesis of compound (A-3)]

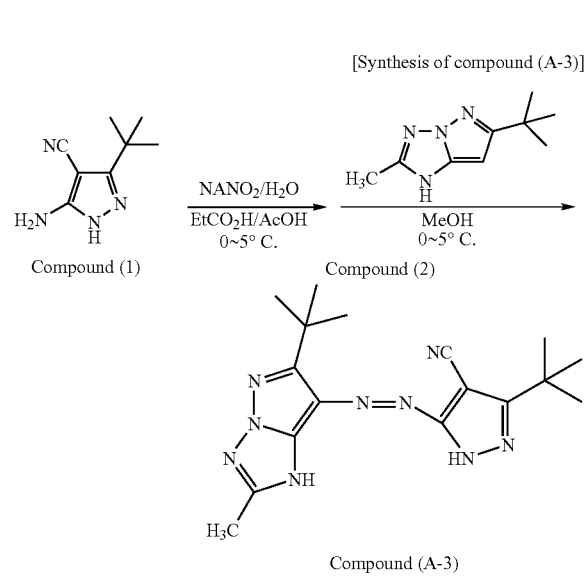

Compound (A-3)

2.6 ml of acetic acid and 4 ml of propionic acid were added to a 100-ml conical flask containing 2 g of a compound (1), and 3.7 ml of a hydrochloric acid (35% to 37%) was slowly added thereto dropwise under ice cooling. The mixture was cooled to 0° C. to 5° C. in an ice bath, and 2 ml of an aqueous solution containing 0.92 g of $NaNO_2$, which had been cooled to 5° C. or lower beforehand, was slowly added thereto dropwise. The resultant mixture was stirred at 0° C. to 5° C. for 15 minutes. Then, 40 ml of a methanol solution containing 2.2 g of a compound (2) was kept at 0° C. to 5° C. under ice cooling, and the above obtained acidic solution was gradually added thereto and stirred for 1 hour. The resultant solution was heated to the room temperature, stirred for 2 hours, and subjected to filtration to isolate the precipitates. The precipitates were washed with a minimum amount of methanol, and purified by a silica gel column chromatography using an eluent of ethyl acetate, to obtain 0.8 g of a compound (A-3).

The obtained compound was identified by 300 MHz $^1$H-NMR. $^1$H-NMR (DMSO-d6) [ppm]; 13.70 (1H, br), 13.5 (1H, s), 2.46 (3H, s), 1.51 (9H, s), 1.44 (9H, s).

Compounds (A-7) and (A-9) were synthesized in the same manner as the compound (A-3). Various azo dyes according to the present invention can be synthesized by the same method. The obtained compounds were identified by 300 MHz $^1$H-NMR. The obtained NMR spectrum data is shown below.

(A-7): $^1$H-NMR (DMSO-d6) [ppm]; 13.95 (2H, br), 2.47 (3H, s), 1.52 (9H, s).

(A-9): $^1$H-NMR (DMSO-d6) [ppm]; 13.45 (2H, br), 10.06 (1H, s), 7.85 (2H, d), 7.52 (1H, t), 7.37 (1H, d), 7.24 (1H, t), 6.82 (2H, d), 3.77 (6H, s), 3.07 (3H, s), 1.44 (9H, s).

Synthesis of azo-metal complexes according to the present invention is described below using example compounds without intention of restricting the scope of the invention.

[Synthesis of (M-1)]

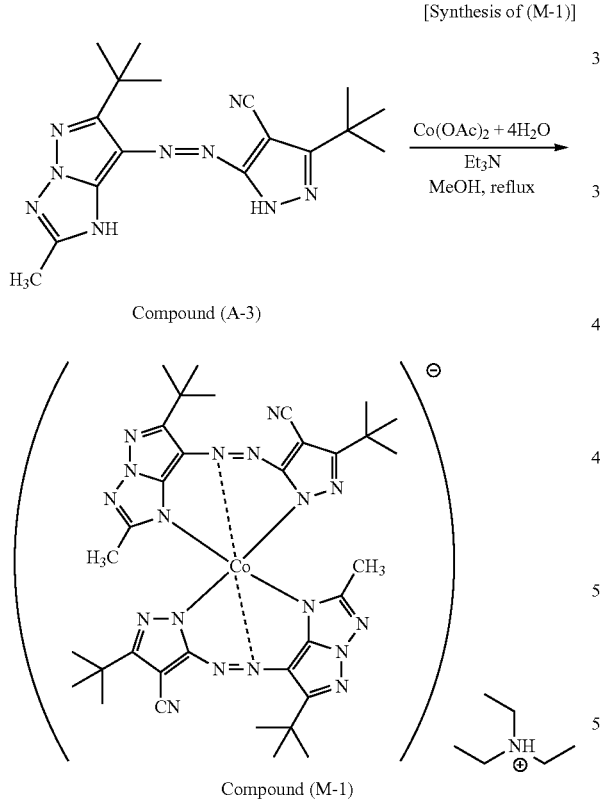

Compound (A-3)

Compound (M-1)

1 g of the compound (A-3) and 20 ml of methanol were added to a 50-ml eggplant-shaped flask, and 2.1 ml of triethylamine was added thereto dropwise while stirring. The mixture was stirred for 10 minutes, and 0.7 g of Co(OAc)$_2$.4H$_2$O was added thereto. The resultant mixture was refluxed under heating for 1 hour. 50 ml of distilled water was added to the mixture, and the mixture was cooled to the room temperature and subjected to filtration to isolate the precipitates. The precipitates were washed with distilled water, and dried to obtain 0.9 g of a compound (M-1). The obtained compound was identified by MALDI-MS; m/z=762 (nega), 102 (posi).

[Synthesis of Compound (M-2)]

A compound (M-2) was synthesized in the same manner as the compound (M-1) except for using Ni(OAc)$_2$.4H$_2$O instead of Co(OAc)$_2$.4H$_2$O. The obtained compound was identified by MALDI-MS; m/z=762 (nega), 102 (posi).

[Synthesis of compound (M-13)]

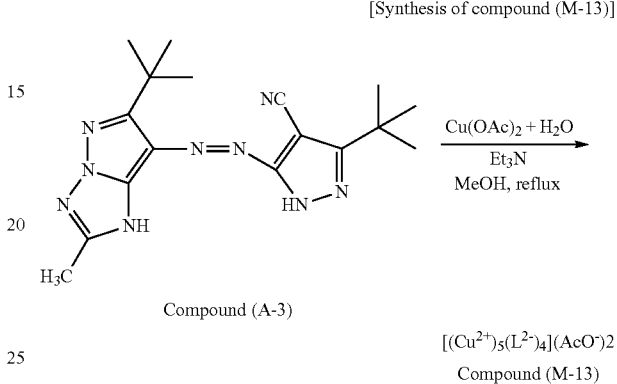

Compound (A-3)

[(Cu$^{2+}$)$_5$(L$^{2-}$)$_4$](AcO$^-$)$_2$

Compound (M-13)

L$^{2-}$ = 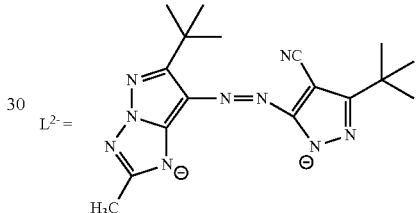

A compound (M-13) was synthesized in the same manner as the compound (M-1) except for using Cu(OAc)$_2$.H$_2$O instead of Co(OAc)$_2$.4H$_2$O. The obtained compound was identified by ESI-MS; m/z=1724.5, 861.7, absorption λmax=440 nm (in acetone). A fragment was detected in MALDI-MS; m/z=893 (nega), 829 (nega), 415 (posi), absorption λmax=440 nm (in acetone).

The obtained compound (M-13) was subjected to an ESR analysis, whereby it was found that the compound (M-13) had a structure containing three N atoms coordinating to the Cu$^{2+}$ ion in the powder state.

A compound (M-21) was synthesized in the same manner as the compound (M-13), and subjected to X-ray structure analysis. As a result, it was found that the compound (M-21) had a structure containing the Cu and the divalent azo dye anion at a ratio of 5:4.

Azo-metal complexes (M-14), (M-15), (M-16), (M-17), etc. containing different anions can be synthesized in the same manner as the compound (M-13) except for using, instead of Cu(OAc)$_2$.H$_2$O, Cu compounds containing the different anions.

Various azo-metal complex dyes according to the present invention can be synthesized by a similar method. The compounds can be identified by MALDI-MS, ESI-MS, ESR analysis, elemental analysis, and X-ray structure analysis.

The azo-metal complex dye, obtained by the same synthesis method as the compound (M-1), can undergo a cation exchange reaction in a solvent. An example of the cation exchange reaction is described below.

[Synthesis of compound (M-6)]

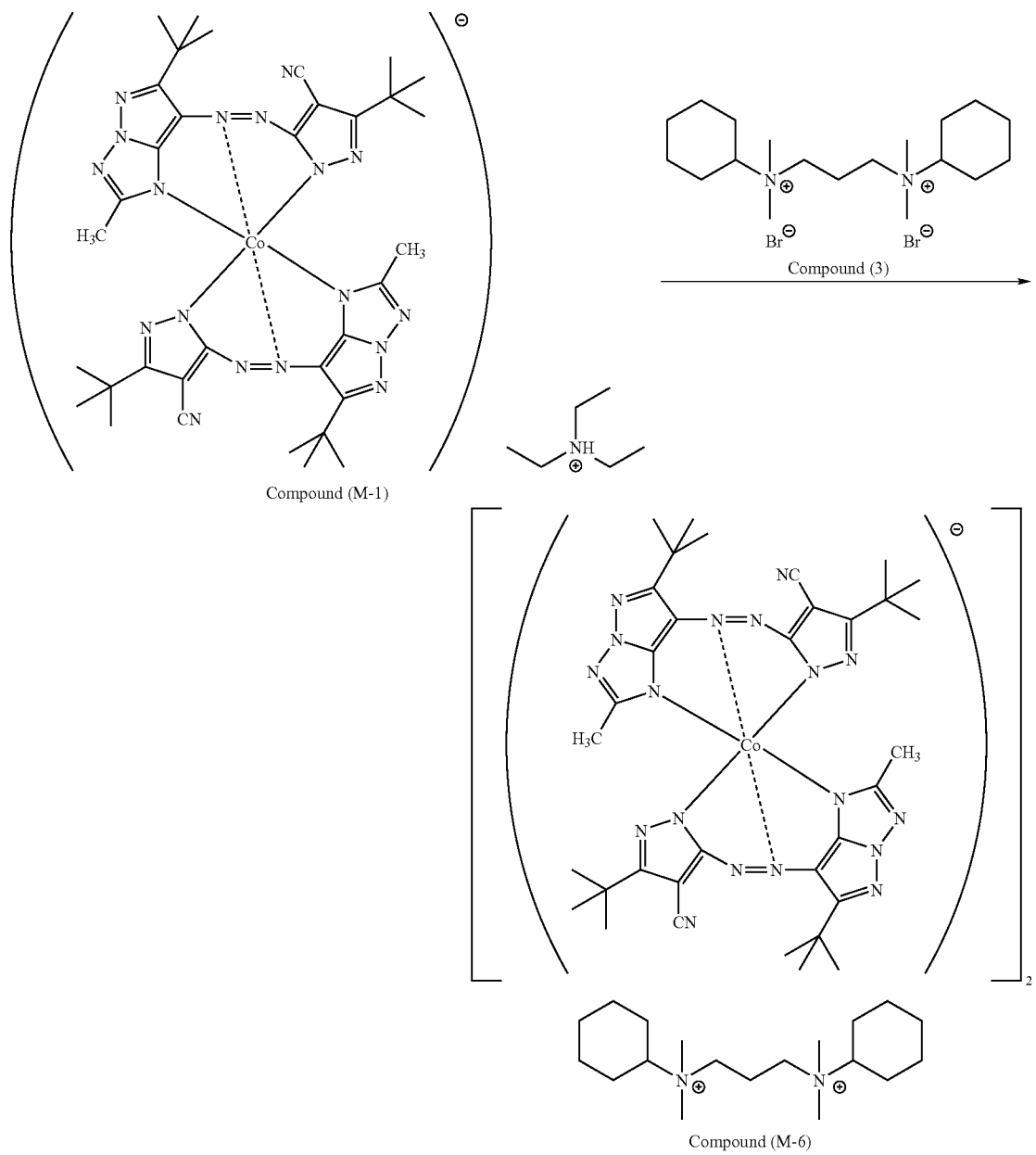

300 mg of the compound (M-1) and 10 ml of methanol were added to a 50-ml eggplant-shaped flask, to which a solution prepared by dissolving 200 mg of a compound (3) in 5 ml of methanol and 5 ml of distilled water was added while stirring. The mixture was refluxed under heating for 1 hour. To the mixture, 20 ml of distilled water was added, and the resultant mixture was cooled to the room temperature. The precipitates were isolated by filtration, washed with distilled water, and dried to obtain 270 mg of a compound (M-6). The obtained compound was identified by MALDI-MS; m/z=762 (nega), 297 (poli).

Various azo-metal complex dyes containing various cations according to the present invention can be synthesized in the same manner as the compound (M-6).

Furthermore, various azo-metal complex dyes containing organic anions such as a compound (M-18) can be synthesized by anion exchange in the same manner as the compound (M-6).

[Synthesis of Comparative Compound (C)]

Comparative compound (C) is included in Japanese Laid-Open Patent Publication No. 2006-142789.

100 mg of a compound (A-3) and 3 ml of methanol were added to a 50-ml eggplant-shaped flask, and 34 mg of $NiCl_2 \cdot 6H_2O$ was added thereto while stirring. The mixture was stirred for 30 minutes, and 20 ml of distilled water was added thereto. The generated precipitates were isolated by filtration, washed with distilled water, and dried to obtain 110 mg of a comparative compound (C). The obtained compound was identified by MALDI-MS; m/z=763.5 (posi).

[Production of Optical Information Recording Medium]
(Preparation of Substrate 12)

A polycarbonate resin substrate having a thickness of 1.1 mm, an outer diameter of 120 mm, and an inner diameter of 15 mm, which had spiral pregrooves 34 with a track pitch of 320 nm, a groove 40 width (a concave portion width) of 190 nm, a groove depth of 47 nm, a groove inclination angle of 65°, and a wobble amplitude of 20 nm, was prepared by injection forming. Mastering of a stamper used in the injection forming was carried out by using a laser cutting (351 nm).

(Formation of Light Reflection Layer 18)

A 60-nm-thick, ANC light reflection layer (containing 98.1 at % of Ag, 0.7 at % of Nd, and 0.9 at % of Cu) was formed as a vacuum-formed film on the substrate 12 by DC sputtering using CUBE manufactured by Unaxis in an Ar atmosphere. The thickness of the light reflection layer 18 was controlled by selecting the sputtering time.

(Formation of Worm-Type Recording Layer 14)

Dye-containing coating liquids of Examples 1 to 10 were prepared by dissolving 1 g of each of the compounds (M-1), (M-13), (M-16), (M-17), (M-22), (M-23), (M-26), (M-32), (M-2), and (M-38) in 100 ml of 2,2,3,3-tetrafluoropropanol. Then, each of the prepared dye-containing coating liquids was applied to the light reflection layer 18 by a spin coating method under conditions of 23° C. and 50% RH while changing the rotation rate within a range of 500 to 2,200 rpm, to form a WORM-type recording layers 14.

The formed WORM-type recording layer 14 was subjected to an annealing treatment in a clean oven. In the annealing treatment, the substrate 12 was supported at 80° C. for 1 hour by a vertical stack pole at a distance kept by a spacer.

(Formation of Barrier Layer 20)

A 10-nm-thick, barrier layer 20 of $Nb_2O_5$ was formed on the WORM-type recording layer 14 by DC sputtering using CUBE manufactured by Unaxis in an Ar atmosphere.

(Sticking of Cover Layer 16)

A polycarbonate film (PUREACE available from Teijin, 80-μm thick), which had an inner diameter of 15 mm and an outer diameter of 120 mm and had a tacky layer (glass-transition temperature −26° C.) on one side, was used as a cover layer 16. The total thickness of the tacky layer and the polycarbonate film was 100 μm.

The cover layer was placed on the barrier layer 20 such that the barrier layer 20 was brought into contact with the tacky layer. Then, the cover layer 16 was pressed by a pressing member, to stick the cover layer 16 on the barrier layer 20. An optical information recording medium 10A having a layer structure shown in FIG. 1 was produced by the above processes.

Optical information recording media of Examples 1 to 10 were produced in this manner respectively.

COMPARATIVE EXAMPLES 1 to 8

Production of Optical Information Recording Medium

Optical information recording media of Comparative Examples 1 to 8 were produced respectively in the same manner except for using comparative dye compounds (A) to (H) instead of the example compound (M-1) in the WORM-type recording layer 14.

For example, in Comparative Example 1, 1 g of the following comparative compound (A) was dissolved in 100 ml of 2,2,3,3-tetrafluoropropanol to prepare a dye-containing coating liquid. The optical information recording medium of Comparative Example 1 was produced in the same manner as Examples 1 to 10 except for the comparative compound (A). Also, the optical information recording media of Comparative Examples 2 to 8 were produced respectively in the same manner as Comparative Example 1 except for using 1 g of the following comparative compounds (B) to (H).

Comparative compound (A), included in Japanese Laid-Open Patent Publication No. 2001-158862

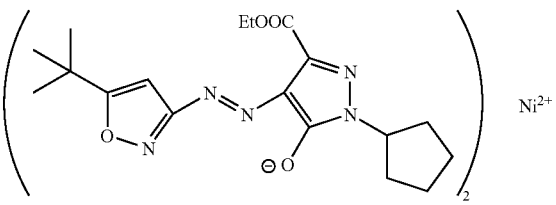

Comparative compound (B), described in Japanese Laid-Open Patent Publication No. 2001-158862

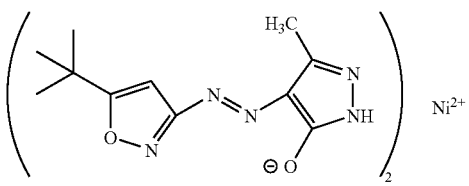

Comparative compound (C), included in Japanese Laid-Open Patent Publication No. 2006-142789

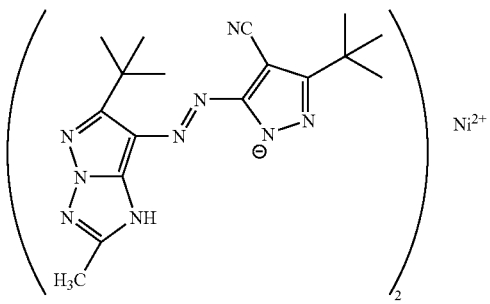

Comparative compound (D), described in Japanese Laid-Open Patent Publication No. 2006-306070

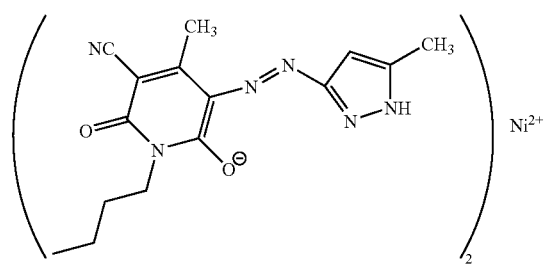

Comparative compound (E), described in Japanese Laid-Open Patent Publication No. 2005-297406

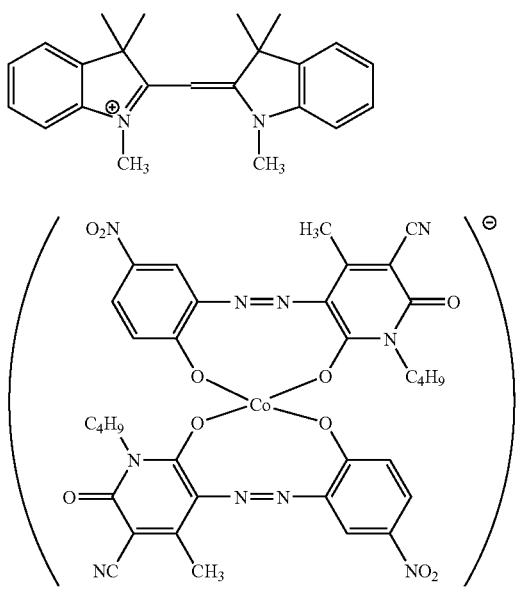

Comparative compound (F), included in Japanese Laid-Open Patent Publication No. 2006-142789

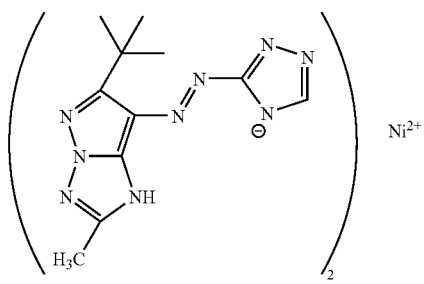

Comparative compound (G), described in Japanese Laid-Open Patent Publication Nos. 2005-297406 and 2005-297407

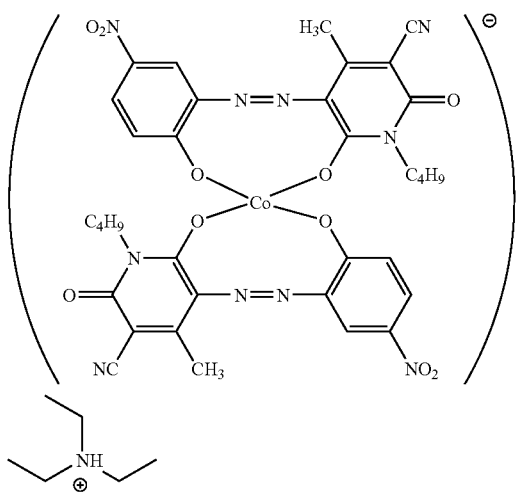

Comparative compound (H), described in Japanese Laid-Open Patent Publication No. 2000-168237

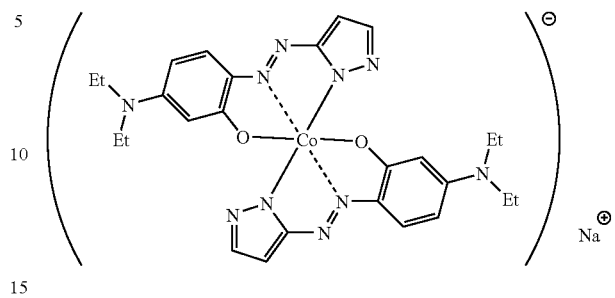

<Evaluation of optical information recording medium>
(1) Evaluation of C/N (carrier-to-noise ratio)

A 0.16-pm signal (2T) was recorded and reproduced in each of the produced optical information recording media by using a recording/reproducing evaluator (DDU1000 manufactured by Pulstec Industrial Co., Ltd.) having 403-nm laser and NA 0.85 pickup under conditions of a clock frequency of 66 MHz and a linear speed of 4.92 m/s. The recorded pit was reproduced by a spectrum analyzer (FSP-3 manufactured by Rohde & Schwarz). An output at 16MHz after recording was used as Carrier output, an output at 16 MHz before recording was used as Noise output, and a C/N value was obtained by the output after recording—the output before recording. In this evaluation, the signal was recorded on the grooves by the optical information recording method according to the present invention. Further, the recording power was 5 to 6 mW, and the reproducing power was 0.3 mW. The results are shown in Table 4. The 2T recording C/N ratio is used as a measure of recording properties. As the recording power is increased, the 2T recording C/N ratio tends to be increased. In view of both the 2T recording C/N ratio and the recording sensitivity, when the C/N ratio (after recording) is 35 dB or more at 5 to 6 mW, the recording medium is considered to have sufficient recording sensitivity and reproduced signal intensity, and thereby have satisfactory recording properties.

(2) Evaluation of Light Fastness of Dye Film

The dye-containing coating liquids according to Examples 1 to 10 and Comparative Examples 1 to 8 were prepared, and each coating liquid was applied to a 1.1-mm-thick glass plate by a spin coating method under conditions of 23° C. and 50% RH while changing the rotation rate within a range of 500 to 1,000 rpm. The dye film was stored for 24 hours under conditions of 23° C. and 50% RH, and then subjected to a light fastness test using a merry-go-round-type light fastness tester (Cell Tester Model III manufactured by Eagle Engineering, equipped with WG320 Filter manufactured by Schott). The absorption spectrum of the dye film was measured using UV-1600PC manufactured by SHIMADZU immediately before the light fastness test and 48 hours after the light fastness test, and the change of the absorbency at the maximum absorption wavelength was evaluated. A dye for an optical information recording medium is required to have remarkably high light fastness in view of maintaining recorded information for a long time. In this test, a light fastness of 85% or more is considered to be practically satisfactory and preferred.

TABLE 4

|  |  | Corresponding general formula | Azo-metal complex dye | Light fastness of dye film[1] | Recording/reproducing properties (2T recording C/N)[2] |
|---|---|---|---|---|---|
| Present Invention | Example 1 | General formula (2-1) | (M-1) | Excellent | Good |
|  | Example 2 | General formula (B) | (M-13) | Excellent | Excellent |
|  | Example 3 | General formula (B) | (M-16) | Excellent | Excellent |
|  | Example 4 | General formula (B) | (M-17) | Excellent | Excellent |
|  | Example 5 | General formula (B) | (M-22) | Excellent | Excellent |
|  | Example 6 | General formula (B) | (M-23) | Excellent | Excellent |
|  | Example 7 | General formula (3-1) | (M-26) | Excellent | Good |
|  | Example 8 | General formula (B) | (M-32) | Excellent | Excellent |
|  | Example 9 | General formula (2-1) | (M-2) | Good | Good |
|  | Example 10 | General formula (B) | (M-38) | Excellent | Good |
| Comparative Example | Comparative Example 1 | — | Compound (A) | Fair | Fair |
|  | Comparative Example 2 | — | Compound (B) | Poor | —[3] |
|  | Comparative Example 3 | — | Compound (C) | Poor | — |
|  | Comparative Example 4 | — | Compound (D) | —[3] | —[3] |
|  | Comparative Example 5 | — | Compound (E) | Excellent | Fair |
|  | Comparative Example 6 | — | Compound (F) | Fair | Fair |
|  | Comparative Example 7 | — | Compound (G) | Excellent | Fair |
|  | Comparative Example 8 | — | Compound (H) | Fair | Poor |

Note:
[1]Evaluated as "Excellent" when the residual dye ratio 48 hours after the irradiation with an Xe light was 90% or more at absorption λmax, evaluated as "Good" when the ratio was 85% or more and less than 90%, evaluated as "Fair" when the ratio was 75% or more and less than 85%, and evaluated as "Poor" when the ratio was less than 75%;
[2]Evaluated as "Excellent" when the 2T recording C/N was 39 dB or more, evaluated as "Good" when the ratio was 35 dB or more and less than 39 dB, evaluated as "Fair" when the ratio was 30 dB or more and less than 35 dB, and evaluated as "Poor" when the ratio was less than 30 dB; and
[3]Measurement or recording could not be carried out because the recording layer could not be sufficiently formed due to poor solubility.

As shown in Table 4, the azo dyes used in Examples 1 to 10 were more excellent in light fastness and recording/reproducing properties as compared with the conventional azo-metal complexes used in Comparative Examples 1 to 8. The optical information recording media of the invention were capable of recording and reproducing even after the irradiation with an Xe light for 55 hours, and thus were excellent in light fastness.

Furthermore, the azo-metal complex dyes of Examples according to the present invention had excellent solubility in the coating solvent, and had excellent stability in film.

Additionally, the azo-metal complex dyes of Examples were more excellent in solution stability in the coating solvent as compared with the compounds of Comparative Examples.

<Evaluation of Light Fastness of Dye Solution>

Each of the azo-metal complex dyes of Examples 1 to 10 was dissolved in 2,2,3,3-tetrafluoropropanol such that the absorbency was 0.95 to 1.05 (cell width 1 cm). The light fastness of thus-obtained solution was evaluated in the same manner as the above dye films. As a result, all the solutions were remarkably excellent in light fastness, and had a residual dye ratio of 90% or more after 48 hours. The light fastness is an important property required for various applications. The compound of the present invention shows excellent light fastness in film and solution, and thereby can show excellent functions in various applications of inks, color filters, color conversion filters, photographic materials, thermal transfer recording materials, and the like.

Furthermore, in a heating and humidifying test, the compound (M-13) was applied to a glass plate by spin coating, stored for 24 hours at a temperature of 80° C. and a relative humidity of 85%, and subjected to the same measurement. As a result, the absorption spectrum was not changed, and thus it was found that the compound was excellent in storability under high temperature and high humidity.

Furthermore, the dyes according to the present invention were not decomposed in the powder or film state even at a temperature of 150° C., and thus were excellent in thermal stability. Therefore, the compound of the present invention can show excellent functions not only in optical information recording media but also in various applications of inks, color filters, color conversion filters, photographic materials, and the like.

It should be noted that the optical information recording medium and the azo-metal complex dye of the present invention are not limited to the above embodiments, and various changes and modifications may be made therein without departing from the scope of the present invention.

The invention claimed is:

1. An optical information recording medium comprising a substrate having a surface with pregrooves with a track pitch of 50 to 500 nm and a recording layer on the surface of the substrate on which information is recorded by irradiation with a laser light having a wavelength of 440 nm or less, wherein the recording layer comprises at least one azo-metal complex dye derived from a metal ion and a compound represented by the following general formula (1-1) or (1-2):

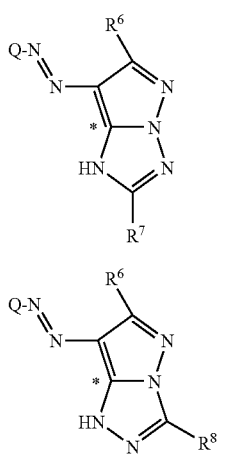

(1-1)

(1-2)

wherein Q represents a carbocyclic group or a heterocyclic group, and $R^6$ to $R^8$ independently represent a hydrogen atom or a substituent, the compound represented by the general formula (1-1) or (1-2) has a dissociative hydrogen atom in Q, and a residue provided by eliminating the dissociative hydrogen atom in Q and the hydrogen atom in the —NH— group marked with asterisk * from the compound represented by the general formula (1-1) or (1-2) is bonded to the metal ion to generate the azo-metal complex dye, and the azo-metal complex dye may contain a component other than the metal ion and the compound represented by the general formula (1-1) or (1-2);

wherein the azo-metal complex dye is represented by the following general formula (A):

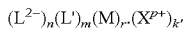

wherein $L^{2-}$ represents a divalent azo dye anion provided by eliminating two hydrogen atoms from the compound represented by the following general formula (1-1) or (1-2):

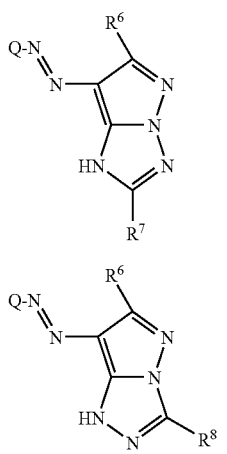

(1-1)

(1-2)

in which Q represents a carbocyclic group or a heterocyclic group, and $R^6$ to $R^8$ independently represent a hydrogen atom or a substituent, L' represents a ligand, M represents a metal ion or a metal oxide ion, n represents an integer of 1 to 4, m represents an integer of 0 to 3, r represents 1 or 2, $X^{p+}$ represents a p-valent cation, p represents an integer of 1 to 10, and k' represents a value within the range of $0 < k' \leq 4$ obtained by dividing the total negative charge of $(L^{2-})_n(L')_m(M)_r$ by p.

2. An optical information recording medium according to claim 1, wherein the azo-metal complex dye is represented by the following general formula (2-1):

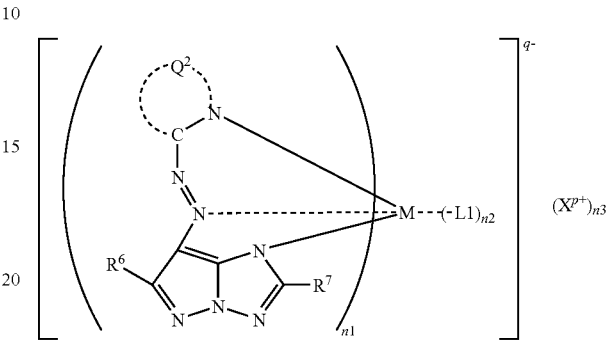

wherein M represents a metal ion or a metal oxide ion, $Q^2$ represents an atomic group forming a heterocycle, L1 represents a ligand, $X^{p+}$ represents a p-valent cation, p represents an integer of 1 to 10, q represents an integer of 1 to 4, n1 represents 1 or 2, n2 represents an integer of 0 to 3, n3 represents a value of q/p within the range of $0 < n3 \leq 4$, and $R^6$ and $R^7$ independently represent a hydrogen atom or a substituent.

3. An optical information recording medium according to claim 1 wherein the azo-metal complex dye is represented by the following general formula (3-1):

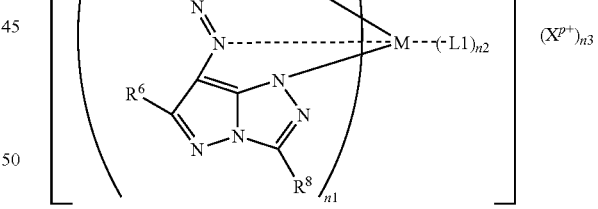

wherein M represents a metal ion or a metal oxide ion, $Q^2$ represents an atomic group forming a heterocycle, L1 represents a ligand, $X^{p+}$ represents a p-valent cation, p represents an integer of 1 to 10, q represents a number of 1 to 4, n1 represents 1 or 2, n2 represents an integer of 0 to 3, n3 represents a value of q/p within the range of $0 < n3 \leq 4$, and $R^6$ and $R^8$ independently represent a hydrogen atom or a substituent.

4. An optical information recording medium according to claim 1, wherein the $X^{p+}$ is an ammonium cation.

5. An optical information recording medium according to claim 1, wherein the metal ion is a copper ion.

6. An optical information recording medium according to claim 1, wherein a reflection layer and the recording layer are stacked in this order on the surface of the substrate having the pregrooves with the track pitch of 50 to 500 nm.

7. An optical information recording medium comprising a substrate having a surface with pregrooves with a track pitch of 50 to 500 nm and a recording layer on the surface of the substrate on which information is recorded by irradiation with a laser light having a wavelength of 440 nm or less, wherein the recording layer comprises at least one azo-metal complex dye derived from a metal ion and a compound represented by the following general formula (1-1) or (1-2):

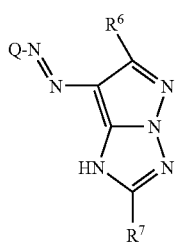
(1-1)

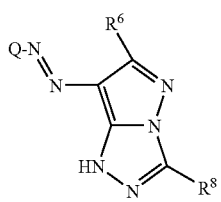
(1-2)

wherein Q represents a carbocyclic group or a heterocyclic group, and $R^6$ to $R^8$ independently represent a hydrogen atom or a substituent, the compound represented by the general formula (1-1) or (1-2) has a dissociative hydrogen atom in Q, and a residue provided by eliminating the dissociative hydrogen atom in Q and the hydrogen atom in the —NH— group marked with asterisk * from the compound represented by the general formula (1-1) or (1-2) is bonded to the metal ion to generate the azo-metal complex dye, and the azo-metal complex dye may contain a component other than the metal ion and the compound represented by the general formula (1-1) or (1-2), wherein the azo-metal complex dye contains the metal ion and a divalent azo dye anion provided by eliminating two hydrogen atoms from the compound represented by the following general formula (1-1) or (1-2):

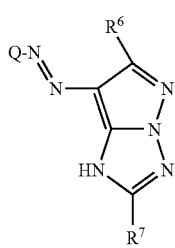
(1-1)

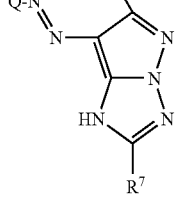
(1-2)

wherein Q represents a carbocyclic group or a heterocyclic group, and $R^6$ to $R^8$ independently represent a hydrogen atom or a substituent, and the number ratio of the divalent azo dye anion to the metal ion is 4/5 in the azo-metal complex dye.

8. An optical information recording medium comprising a substrate having a surface with pregrooves with a track pitch of 50 to 500 nm and a recording layer on the surface of the substrate on which information is recorded by irradiation with a laser light having a wavelength of 440 nm or less, wherein the recording layer comprises at least one azo-metal complex dye derived from a metal ion and a compound represented by the following general formula (1-1) or (1-2):

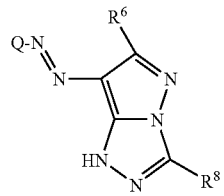
(1-1)

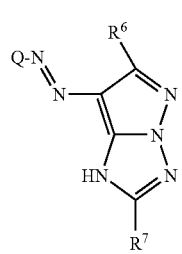
(1-2)

wherein Q represents a carbocyclic group or a heterocyclic group, and $R^6$ to $R^8$ independently represent a hydrogen atom or a substituent, the compound represented by the general formula (1-1) or (1-2) has a dissociative hydrogen atom in Q, and a residue provided by eliminating the dissociative hydrogen atom in Q and the hydrogen atom in the —NH— group marked with asterisk * from the compound represented by the general formula (1-1) or (1-2) is bonded to the metal ion to generate the azo-metal complex dye, the azo-metal complex dye contains the metal ion and a divalent azo dye anion provided by eliminating two hydrogen atoms from the compound represented by the following general formula (1-1) or (1-2):

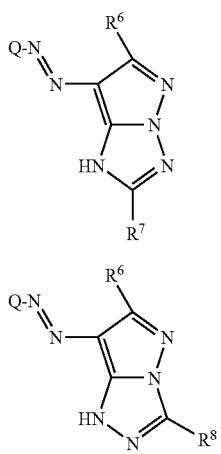

wherein Q represents a carbocyclic group or a heterocyclic group, and $R^6$ to $R^8$ independently represent a hydrogen atom or a substituent, and
the number ratio of the divalent azo dye anion to the metal ion is at most 1/1 in the azo-metal complex dye; and
wherein the azo-metal complex dye is represented by the following general formula (B):

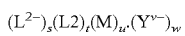

wherein $L^{2-}$ represents the divalent azo dye anion provided by eliminating two hydrogen atoms from the compound represented by the following general formula (1-1) or (1-2):

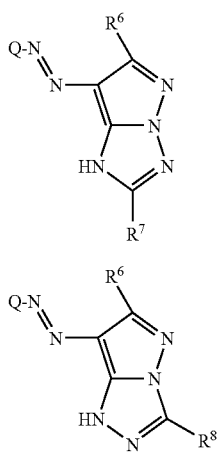

in which Q represents a carbocyclic group or a heterocyclic group, and $R^6$ to $R^8$ independently represent a hydrogen atom or a substituent, L2 represents a ligand, M represents a metal ion or a metal oxide ion, s represents an integer of 1 to 4, t represents an integer of 0 to 14, u represents an integer of 2 to 5, $Y^{v-}$ represents a v-valent anion, v represents an integer of 1 to 10, and w represents a value within the range of $0<w\leq 4$ obtained by dividing the total positive charge of $(L^{2-})_s(L2)_t(M)_u$ by v.

9. An azo-metal complex dye represented by the following general formula (C):

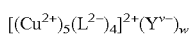

wherein $L^{2-}$ represents a divalent azo dye anion provided by eliminating two hydrogen atoms from a compound represented by the following general formula (1-1) or (1-2):

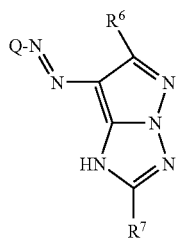

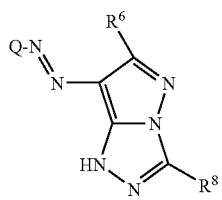

in which Q represents a substituted or unsubstituted pyrazole ring group, and $R^6$ to $R^8$ independently represent a substituted or unsubstituted alkyl group or a substituted or unsubstituted aryl group, and $(Y^{v-})_w$ represents $(Cl^-)_2$, $(Br^-)_2$, $(I^-)_2$, $(ClO_4^-)_2$, $(PF_6^-)_2$, $(BF_4^-)_2$, $SO_4^{2-}$ or $(CH_3COO^-)_2$.

10. An azo-metal complex dye comprising five Cu ions, four divalent azo dye anions and a counterpart ion $(Y^{v-})_w$, the four divalent azo dye anions being provided by eliminating two hydrogen atoms from a compound represented by the following general formula (1-1) or (1-2):

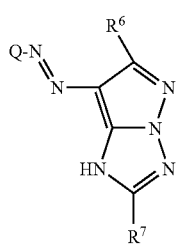

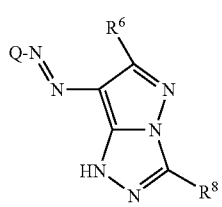

in which Q represents a substituted or unsubstituted pyrazole ring group, and $R^6$ to $R^8$ independently represent a substituted or unsubstituted alkyl group or a substituted or unsubstitued aryl group, and wherein the counterpart ion $(Y^{v-})_w$ represents $(Cl^-)_2$, $(Br^-)_2$, $(I^-)_2$, $(ClO_4^-)_2$, $(PF_6^-)_2$, $(BF_4^-)_2$, $SO_4^{2-}$ or $(CH_3COO^-)_2$.

11. An azo-metal complex dye represented by the following general formula (B):

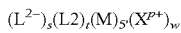

wherein $L^{2-}$ represents a divalent azo dye anion provided by eliminating two hydrogen atoms from a compound represented by the following general formula (1-1) or (1-2):

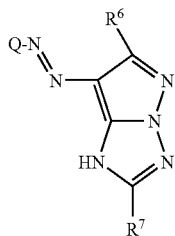
(1-1)

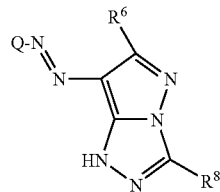
(1-2)

in which Q represents a substituted or unsubstituted pyrazole ring group, $R^6$ to $R^8$ independently represent a substituted or unsubstituted alkyl group or a substituted or unsubstituted aryl group, L2 represents a ligand, M represents a copper ion, s represents an integer of 1 to 4, t represents an integer of 0 to 14, and at least one copper ion is $Cu^{2+}$ and other copper ions are $Cu^+$, $X^{p+}$ represents a p-valent cation, p represents an integer of 1 to 10, and w represents a value within a range of $0<w\leq 4$ obtained by dividing the total negative charge of $(L^{2-})_s(L2)_t(M)_5$ by p.

* * * * *